US012629259B2

(12) United States Patent
Gorelick

(10) Patent No.: US 12,629,259 B2
(45) Date of Patent: May 19, 2026

(54) METHOD AND APPARATUS FOR JOINT REPLACEMENT ARTHROPLASTY

(71) Applicant: FIBIOSEQ MEDICAL LTD., Rosh-Hanikra (IL)

(72) Inventor: Lauren Gorelick, Rosh-Hanikra (IL)

(73) Assignee: FIBIOSEQ MEDICAL LTD., Rosh-Hanikra (IL)

( * ) Notice: Subject to any disclaimer, the term of this patent is extended or adjusted under 35 U.S.C. 154(b) by 630 days.

(21) Appl. No.: 18/074,480

(22) Filed: Dec. 4, 2022

(65) Prior Publication Data

US 2023/0101398 A1 Mar. 30, 2023

Related U.S. Application Data

(63) Continuation of application No. 17/866,639, filed on Jul. 18, 2022, which is a continuation of application (Continued)

(51) Int. Cl.
*A61F 2/42* (2006.01)
*A61B 17/80* (2006.01)
(Continued)

(52) U.S. Cl.
CPC ........ *A61F 2/4261* (2013.01); *A61B 17/8061* (2013.01); *A61B 17/809* (2013.01); *A61B 17/86* (2013.01); *A61F 2002/30131* (2013.01); *A61F 2002/30156* (2013.01); *A61F 2002/30192* (2013.01); *A61F 2002/30387* (2013.01); *A61F 2002/30405* (2013.01);
(Continued)

(58) Field of Classification Search
CPC .......... A61F 2/4261–2002/4297; A61F 2/4606
See application file for complete search history.

(56) References Cited

U.S. PATENT DOCUMENTS

| 4,307,473 A | * | 12/1981 | Weber | ................... | A61F 2/4261 |
| | | | | | D24/155 |
| 5,314,485 A | * | 5/1994 | Judet | ..................... | A61F 2/4261 |
| | | | | | 623/21.13 |

(Continued)

FOREIGN PATENT DOCUMENTS

| CN | 103735305 A | | 4/2014 | |
| CN | 203524812 U | * | 4/2014 | ........... A61F 2/4261 |

(Continued)

*Primary Examiner* — Alvin J Stewart
(74) *Attorney, Agent, or Firm* — Ballard Spahr LLP

(57) ABSTRACT

A radiocarpal wrist joint replacement includes a radial member configured to be affixed to a portion of an end of the radial bone proximal to the wrist including a fixture to be affixed over a longitudinal aspect of the radial bone and a radial resurfacing plate having a substantially concave surface configured to be located at the end of the radial bone. A carpal capitate bone insert configured to be inserted and affixed into the carpal capitate bone. A bulbous component includes a first convex head and a second convex head, substantially opposite each other and connected by a neck between the first and the second convex head. The radial resurfacing plate of the radial member with the concave surface is configured to be operably coupled to the second convex head of the bulbous component so as to allow radial freedom of motion in the joint replacement.

9 Claims, 19 Drawing Sheets

Related U.S. Application Data

No. 16/082,539, filed as application No. PCT/IL2017/050285 on Mar. 8, 2017, now abandoned, which is a continuation of application No. 15/064,673, filed on Mar. 9, 2016, now Pat. No. 9,717,599.

(51) Int. Cl.
| | |
|---|---|
| *A61B 17/86* | (2006.01) |
| *A61F 2/30* | (2006.01) |

(52) U.S. Cl.
CPC ............... *A61F 2002/30471* (2013.01); *A61F 2002/305* (2013.01); *A61F 2002/30578* (2013.01); *A61F 2002/30604* (2013.01); *A61F 2002/30878* (2013.01); *A61F 2002/30899* (2013.01); *A61F 2002/4264* (2013.01); *A61F 2002/4266* (2013.01); *A61F 2002/4269* (2013.01); *A61F 2002/4282* (2013.01); *A61F 2002/4292* (2013.01); *A61F 2230/0013* (2013.01); *A61F 2230/0054* (2013.01); *A61F 2310/00017* (2013.01); *A61F 2310/00023* (2013.01); *A61F 2310/00161* (2013.01); *A61F 2310/00179* (2013.01)

(56) References Cited

U.S. PATENT DOCUMENTS

| | | | | |
|---|---|---|---|---|
| 5,951,604 | A | 9/1999 | Scheker | |
| 6,485,520 | B1 * | 11/2002 | Hubach | A61F 2/4261 623/21.13 |
| 8,366,784 | B2 | 2/2013 | Palmer | |
| 8,562,689 | B2 | 10/2013 | Scheker | |
| 8,641,770 | B2 * | 2/2014 | Scheker | A61F 2/4241 623/21.16 |
| 8,814,945 | B2 * | 8/2014 | Linares | A61F 2/4261 623/21.13 |
| 9,717,599 | B1 * | 8/2017 | Gorelick | A61F 2/4261 |
| 9,730,797 | B2 * | 8/2017 | Gonzalez-Hernandez | A61F 2/30 |
| 9,962,261 | B1 * | 5/2018 | Scheker | A61F 2/3804 |
| 10,918,493 | B2 * | 2/2021 | Gorelick | A61F 2/30749 |
| 2010/0121390 | A1 | 5/2010 | Kleinman | |
| 2011/0066250 | A1 | 3/2011 | Palmer | |
| 2012/0136453 | A1 * | 5/2012 | Scheker | A61F 2/4261 623/21.12 |
| 2013/0197655 | A1 | 8/2013 | Scheker | |
| 2013/0297033 | A1 | 11/2013 | Kleinman et al. | |
| 2014/0121709 | A1 | 5/2014 | Gonzalez-Hernandez | |
| 2014/0121779 | A1 * | 5/2014 | Gonzalez-Hernandez | A61F 2/4612 623/18.11 |
| 2014/0364957 | A1 | 12/2014 | Palmer | |
| 2017/0290670 | A1 | 10/2017 | Gorelick | |
| 2017/0296350 | A1 * | 10/2017 | Orbay | A61F 2/30734 |
| 2020/0306051 | A1 * | 10/2020 | Stockmans | A61F 2/4241 |
| 2021/0045890 | A1 * | 2/2021 | Zhu | A61F 2/4261 |
| 2022/0346966 | A1 * | 11/2022 | Gorelick | A61F 2/4261 |
| 2023/0101398 | A1 | 3/2023 | Gorelick | |

FOREIGN PATENT DOCUMENTS

| | | | | |
|---|---|---|---|---|
| CN | 115040294 | A * | 9/2022 | ............... A61F 2/30 |
| CN | 119454297 | A * | 2/2025 | ......... A61F 2/30721 |
| EP | 3531982 | B1 * | 2/2022 | ........... A61F 2/4261 |
| WO | WO-2017024336 | A1 * | 2/2017 | ......... A61F 2/30749 |
| WO | 2018077421 | A1 | 5/2018 | |

* cited by examiner

817

815

830

815

710

817

820

815

815

*FIG. 17A*
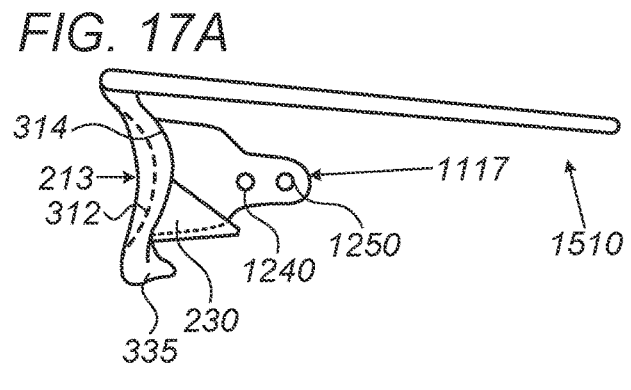
*FIG. 17E*
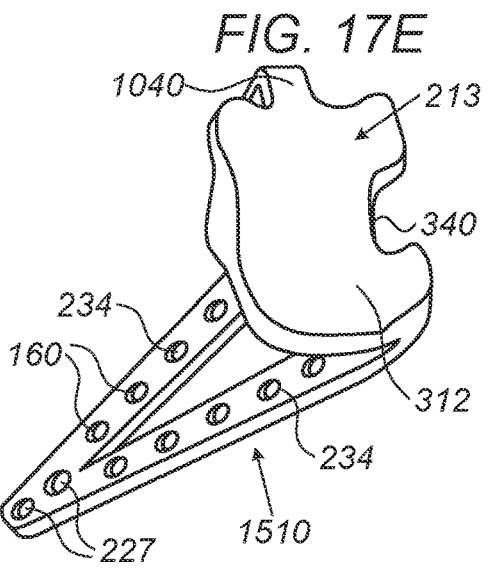
*FIG. 17B*
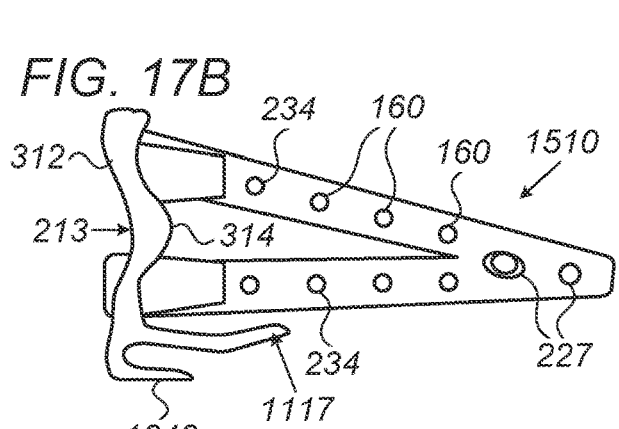
*FIG. 17C*
*FIG. 17D*
*FIG. 17F*
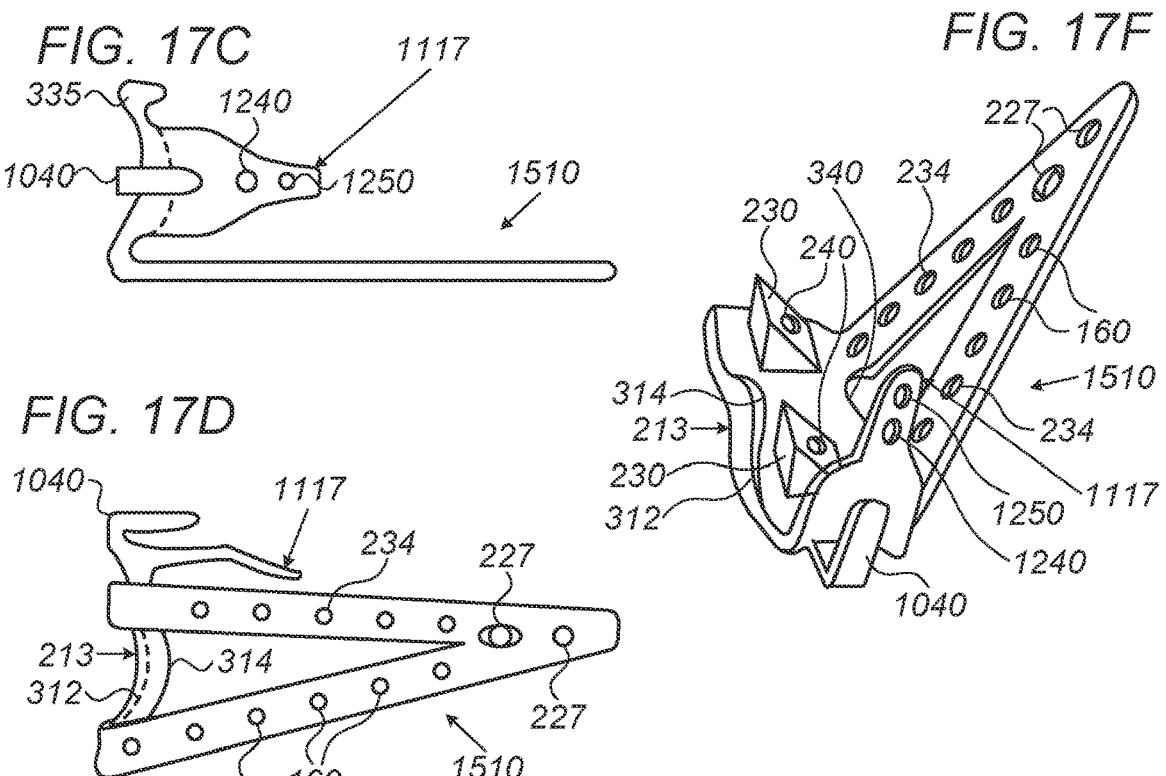

METHOD AND APPARATUS FOR JOINT REPLACEMENT ARTHROPLASTY

CROSS-REFERENCE OF RELATED APPLICATIONS

The present invention is a continuation application of U.S. patent application Ser. No. 17/866,639, filed on Jul. 18, 2022, which was a continuation application of U.S. patent application Ser. No. 16/082,539, filed on Sep. 6, 2018, which was a national phase application of PCT/IL2017/050285, filed on Mar. 8, 2017, claiming priority benefit from U.S. patent application Ser. No. 15/064,673, filed on Mar. 9, 2016 (now U.S. Pat. No. 9,717,599), all of which are incorporated herein by reference in their entirety.

FIELD OF THE INVENTION

The present invention relates to medical implants. More specifically, the present invention relates to a method and an apparatus for joint replacement arthroplasty.

BACKGROUND OF THE INVENTION

A human joint is an interface that bridges two or more bones, and permits a variety of movements between the two or more bones at the joint. A wrist joint, or a knee joint, for example, include bones that intercommunicate in a common synovial cavity. Wrist articulations work together to allow for a wide range of motions in the joint. Most of the wrist motion, for example, occurs in the radiocarpal joint (RCJ) and the distal radioulnar joint (DRUJ). Most of the knee motion occurs in the tibiofemoral joint.

Different joint pathologies may occur in the bones or joints resulting from conditions such as osteoarthritis, or from traumas, such as bone fractures, for example. A patient, or subject, with these joint pathologies may experience severe pain during movements of the joint ranging to severe disabilities due to limitations in joint movements.

When severe joint pathologies occur, therapeutic methods such as the use of medications may not alleviate the pain and movement limitations in the joints of the patient. Partial or full joint replacement arthroplasty may be the best course of treatment for the patient.

SUMMARY OF THE INVENTION

There is thus provided, in accordance with some embodiments of the present invention, a radiocarpal joint replacement apparatus for implantation in a wrist of a subject, including a radial member configured to be affixed to a portion of an end of the radial bone proximal to the wrist including a fixture to be affixed over a longitudinal aspect of the radial bone and a radial resurfacing plate having a substantially concave surface configured to be located at the end of the radial bone, a carpal capitate bone insert configured to be inserted and affixed into the carpal capitate bone, and a bulbous component comprising a first convex head and a second convex head, substantially opposite each other and connected by a neck defining an annular groove between the first convex head and the second convex head, wherein the carpal capitate bone insert is configured to be flexibly coupled to the first convex head of the bulbous component, and wherein the radial resurfacing plate of the radial member with the concave surface is configured to be operably coupled to the second convex head of the bulbous component so as to allow radial freedom of motion of the carpal capitate member with respect to the radial resurfacing plate after the implantation.

Furthermore, in accordance with some embodiments of the present invention, the carpal capitate bone insert includes a dorsal cortical plate and an intraosseous stem, the intraosseous stem inserted into the carpal capitate bone, and the carpal capitate bone insert is affixed to the carpal capitate bone with screws inserted through holes in the dorsal cortical plate and the intraosseous stem.

Furthermore, in accordance with some embodiments of the present invention, the carpal capitate bone insert includes a screw threaded into the carpal capitate bone so as to affix the carpal capitate insert to the carpal capitate bone.

Furthermore, in accordance with some embodiments of the present invention, the carpal capitate bone insert includes petals configured to be inserted into the annular grove so as to flexibly hold the bulbous component to the carpal capitate bone insert.

Furthermore, in accordance with some embodiments of the present invention, the carpal capitate bone insert includes an implant insertion element coated with hydroxy-lapatite.

Furthermore, in accordance with some embodiments of the present invention, the bulbous component is formed from a material selected from the group consisting of polyethylene, ceramic, and pyrocarbon.

Furthermore, in accordance with some embodiments of the present invention, the radial resurfacing plate is formed from a polished metal surface.

Furthermore, in accordance with some embodiments of the present invention, the fixture is V-shaped.

Furthermore, in accordance with some embodiments of the present invention, the radiocarpal joint replacement apparatus, includes a hook formed on the radial member facing the ulna bone and proximal to the wrist, and an ulnar member configured to be affixed to a portion of an end of the ulna bone proximal to the wrist and opposite to the hook, the ulnar member including a bore configured to receive hook, and retain the hook after implantation, wherein the bore is shaped to allow relative movement between the radial bone and the ulna bone so as to facilitate supination and pronation movement of the wrist of the subject.

Furthermore, in accordance with some embodiments of the present invention, the ulnar member is formed from a receptacle piece and a mounting piece.

Furthermore, in accordance with some embodiments of the present invention, the bore is C-shaped.

There is further provided, in accordance with some embodiments of the present invention, a distal radioulnar joint replacement apparatus for implantation in a wrist of a subject, including a sigmoidal member configured to be affixed onto a portion of an end of the radial bone proximal to the wrist including a lower mounting bracket to be affixed over a longitudinal aspect of the radial bone so as to face the ulna bone, the sigmoidal member including a hook, and an ulnar member configured to be affixed to a portion of an end of the ulna bone proximal to the wrist and opposite to the sigmoidal member, the ulnar member including a bore configured to receive hook, and retain the hook after implantation, wherein the bore is shaped so as to allow relative movement between the radial bone and the ulna bone so as to facilitate supination and pronation movement of the wrist of the subject.

Furthermore, in accordance with some embodiments of the present invention, the sigmoidal member includes a triangular peg implanted into cancellous bone at the end of the radius bone.

Furthermore, in accordance with some embodiments of the present invention, the bore is C-shaped.

Furthermore, in accordance with some embodiments of the present invention, the ulnar member is formed from a receptacle piece and a mounting piece.

Furthermore, in accordance with some embodiments of the present invention, the receptacle piece is formed from a material selected from the group consisting of mobile polyethylene and pyrocarbon, and the mounting piece is formed from a material selected from the group consisting of stainless steel and titanium.

There is further provided, in accordance with some embodiments of the present invention, a radiocarpal joint cartilage replacement apparatus for implantation in a wrist of a subject including a radial member configured to be affixed to a portion of an end of the radial bone proximal to the wrist including a fixture to be affixed over a longitudinal aspect of the radial bone and a radial resurfacing plate having a substantially concave surface configured to be located at the end of the radial bone, and a cartilage replacement member with a first surface and a second surface wherein after implantation, the first surface is configured to be operably coupled to the carpal bones in the wrist and configured to be affixed to the radial member on the second surface.

Furthermore, in accordance with some embodiments of the present invention, the cartilage replacement member is configured to be affixed to the radial member on the second surface by one or more tabs formed on the cartilage replacement member that are respectively inserted and held within one or more holes formed in the radial member.

Furthermore, in accordance with some embodiments of the present invention, the cartilage replacement member is formed from plastic.

Furthermore, in accordance with some embodiments of the present invention, the fixture is V-shaped.

There is further provided, in accordance with some embodiments of the present invention, a joint replacement apparatus for implantation into an articulation between a first and a second bone in a subject, the apparatus includes a first member and a second member. The first member is configured to be affixed to an end of the first bone proximal to the articulation between the first bone and the second bone. The first member includes one or more first member fixtures to be affixed externally to cortical bone tissue along a longitudinal aspect of the first bone, and a first resurfacing plate configured to be located at the end of the first bone. The second member is configured to be affixed to an end of a second bone proximal to the articulation. The second member may include one or more second member fixtures configured to be affixed externally to cortical bone tissue along a longitudinal aspect of the second bone, and a second resurfacing plate configured to be located at the end of the second bone, where each of the first and the second resurfacing plates are shaped, to fit and to move together, so as to facilitate anatomical movements of the articulation.

Furthermore, in accordance with some embodiments of the present invention, the articulation includes a proximal interphalangeal joint, the first bone includes a middle phalange bone, and the second bone includes a proximal phalange bone.

Furthermore, in accordance with some embodiments of the present invention, the articulation includes a tibiofemoral joint, the first bone includes a femur bone, and the second bone includes a tibia bone.

Furthermore, in accordance with some embodiments of the present invention, the articulation comprises a radiocarpal joint (RCJ), the first bone comprises a carpal capitate bone, the first member fixture comprises a cortical plate, the first resurfacing plate comprises a convex head of a bulbous component, the second bone comprises a radius bone, the second member fixture comprises a radial fixture, and the second resurfacing plate comprises a radial articular resurfacing plate.

Furthermore, in accordance with some embodiments of the present invention, the one or more first member fixtures and the one or more are second member fixtures are configured to be externally affixed to cortical bone tissue along a longitudinal aspect of the respective first and second bone by screwing screws into screw holes in each of the fixtures.

Furthermore, in accordance with some embodiments of the present invention, wherein the first resurfacing plate and the second resurfacing plate are configured to be affixed to the end of the respective first and second bone proximal to the articulation by screwing screws through screw holes respectively in the one or more first member fixtures and the one or more second member fixtures into peg holes in pegs attached respectively into the first or the second resurfacing plates.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

FIG. 17A schematically illustrates a first side view of a modified radial member, in accordance with some embodiments of the present invention;

FIG. 17B schematically illustrates a bottom view of a modified radial member with a hook, in accordance with some embodiments of the present invention;

FIG. 17C schematically illustrates a second side view of a modified radial member with a hook, in accordance with some embodiments of the present invention;

FIG. 17D schematically illustrates a top view of a modified radial member with a hook, in accordance with some embodiments of the present invention;

FIG. 17E schematically illustrates a first perspective view of a modified radial member with a hook, in accordance with some embodiments of the present invention;

FIG. 17F schematically illustrates a second perspective view of a modified radial member with a hook, in accordance with some embodiments of the present invention;

DETAILED DESCRIPTION OF THE INVENTION

Figure 1:
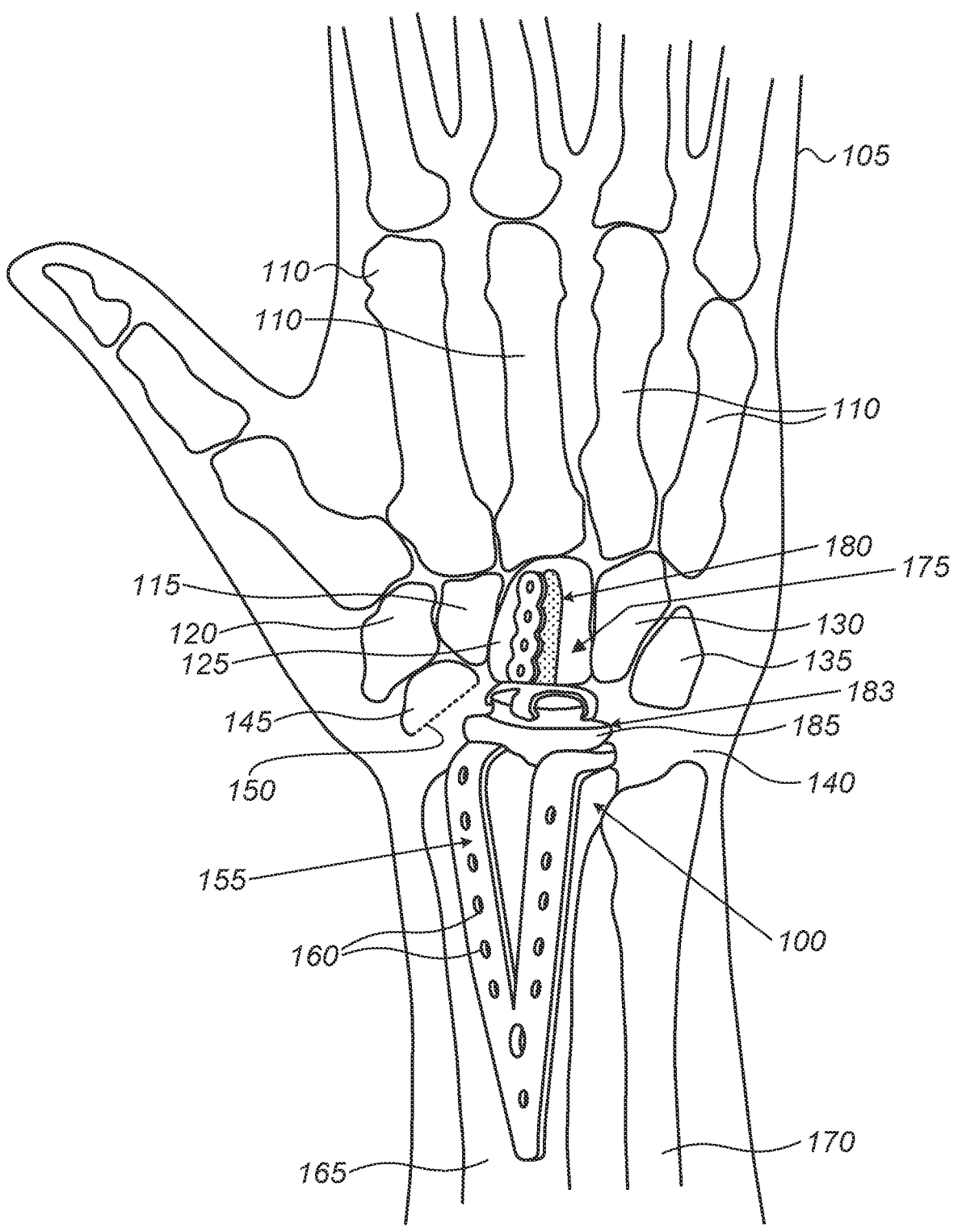
FIG. 1 schematically illustrates a dorsal view of a hand with a radiocarpal joint (RCJ) replacement, in accordance with some embodiments of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining." "establishing". "analyzing". "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example. "multiple" or "two or more". The terms "plurality" or "a plurality" may be used throughout the specification to describe two or more components, devices, elements, units, parameters, or the like.

Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

Previously, different wrist implant topologies involved the resection of portions of the radius and/or ulna bones and affixing portions of the implant components, such as pegs, within the soft intramedullary canal. Such soft tissue stabilizing techniques of the implant components in the soft medullary tissue have been shown to loosen over time and ultimately fail, which requires additional surgery to fix and re-stabilize the implants. Moreover, in some implant topologies, the implant components may be bolted across multiple carpal bones to fix the multiple carpal bones in place severely limiting wrist movements. Some implants may bond portions of the radius to the ulna particularly in the case after large resections of those bones. These implant topologies severely limit the motion in the multiple wrist joints and may cause early loosening of the implant.

Described herein are some embodiments of a method and apparatus for wrist arthroplasty including radiocarpal joint (RCJ) and distal radioulnar joint (DRUJ) replacements. A method and apparatus for renewing the articular surface of the distal radius with a cartilage replacement can be used to repair damage, for example, from intra-articular fractures of the distal radius (e.g., from sport injuries) according to some embodiments of the present invention is also taught herein without the need to replace the entire joint (e.g., hemi-arthroplasty). Implant solutions according to some embodiments of the present invention overcome many of the implant failure and joint mobility problems seen in previous wrist implants and prostheses.

Wrist implants according to some embodiments of the present invention further account for minimal bone resection, preservation of the mobility of the radiocarpal, intercarpal and carpometacarpal joints, and a reduction of shear, bending and frictional forces in the implant components so as to prevent a loosening of the implant. Wrist implant topologies according to some embodiments of the present invention do not apply a classic ball and socket approach to the joint, but apply methods of joint articular surface reconstruction to the complex joint surfaces. Implant technologies according to some embodiments of the present invention include wrist implant topologies which combine radiocarpal joint (RCJ) replacement with the option of DRUJ resurfacing replacement and stabilization within the same implant.

Implant topologies according to some embodiments of the present invention utilize a plate fixation method whereby the implant components are plate-like and use screws to affix the plate components to the hard outer cortical bone layers for better implant stability. There is minimal bone resection with minimal placement of the implant components within the soft issue of the medullary cavity to stabilize the implant. Plate-like components used in some embodiments of the present invention employ a closed frame construction, such as the Y-plate affixed to the radius used in the RCJ implant as will described later, so as to achieve maximum contact and mechanical stability of the implant with prevention of implant failure. Surgical techniques employed according to some embodiments of the present invention for implanting the wrist replacements are simple and easy.

FIG. 1 schematically illustrates a dorsal view of a hand 105 with a first embodiment of a radiocarpal joint (RCJ) replacement 100, in accordance with some embodiments of the present invention. Hand 105 includes metacarpal bones 110, and the carpal bones, or carpus, including carpal trapezoid bone 115, carpal trapezium bone 120, carpal capitate bone 125, carpal hamate bone 130, and carpals triquetral/pisiform bones 135.

To implant the RCJ replacement shown in FIG. 1 in the wrist of hand 105, the carpal lunate bone is removed from a region 140 from hand 105. A carpal scaphoid bone 145 is surgically cut along a cut plane 150 and cartilage is removed from the RCJ. Radius bone 165 and ulna bone 170 are shown in FIG. 1.

A radial member 155 of the RCJ replacement includes holes 160 through which fasteners, typically screws, are to be inserted and threaded to allow affixing, attaching, or locking radial member 155 to a portion of an end of radius bone 165 proximal to the wrist. In contrast to the problems associated with soft tissue mounting of implants, radial member 155 is typically affixed to the cortex of radius bone 165 (e.g., cortical bone tissue of the radius bone) so as to provide a solid mechanical support for the RCJ replacement.

A carpal capitate member 175 includes a carpal capitate bone insert 180 and a bulbous component 183. Carpal bone insert 180 of the RCJ replacement is configured to be inserted and affixed only to carpal capitate bone 125 of the wrist, but not to other carpal bones, allowing greater maneuverability of the wrist, as a result. Carpal capitate bone insert 180 is coupled to bulbous component 183, which includes a convex head 185 substantially opposite to carpal capitate bone insert 180.

Figure 2:
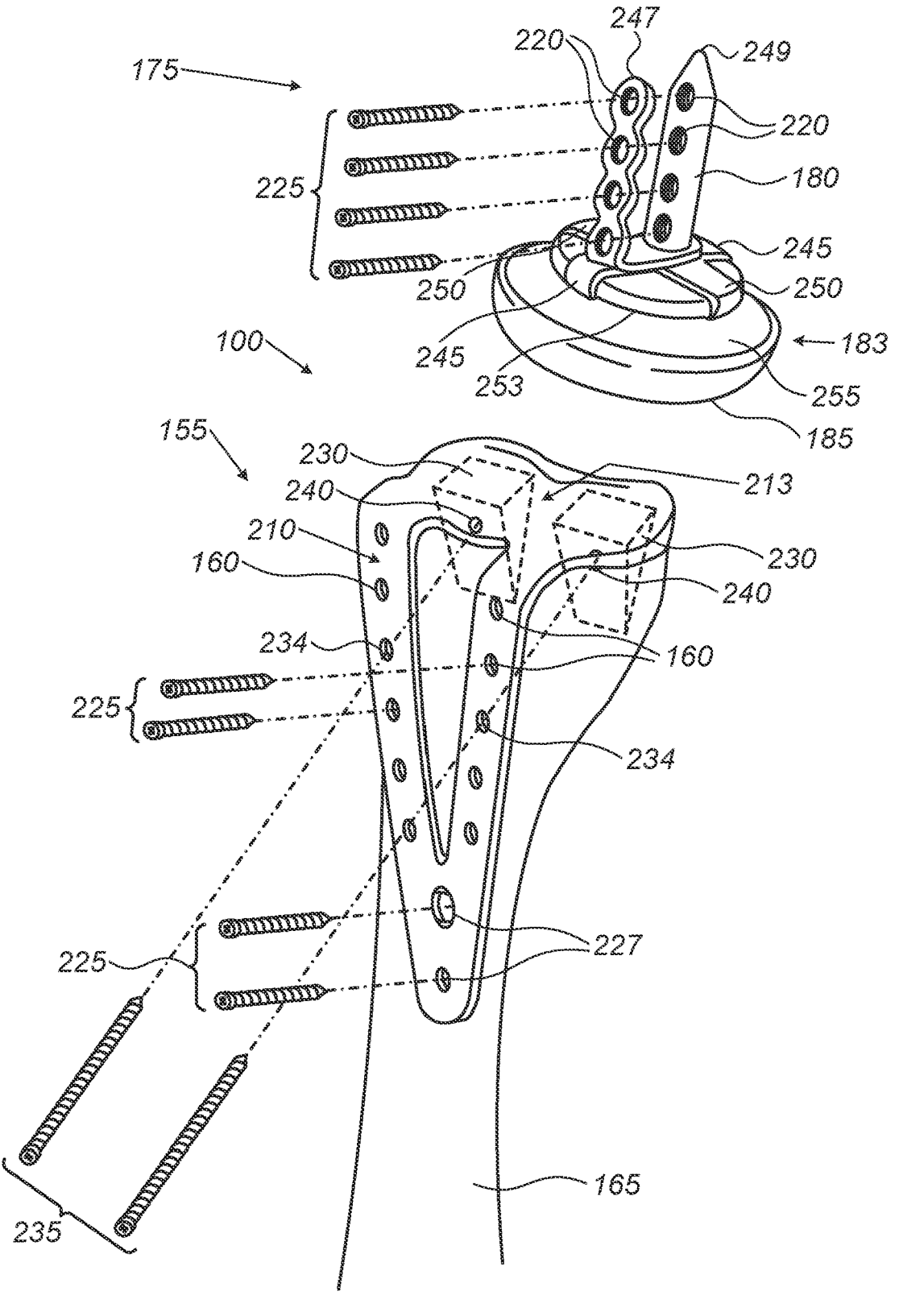
FIG. 2 schematically illustrates an exploded view of a radiocarpal joint (RCJ) replacement, in accordance with some embodiments of the present invention.

FIG. 2 schematically illustrates an exploded view of radiocarpal joint (RCJ) replacement 100, in accordance with some embodiments of the present invention. Radial member 155 of the radiocarpal joint (RCJ) replacement includes a radial fixture 210 to be affixed over a longitudinal aspect of the radial bone. Radial fixture 210 may have various forms, designed to match and provide good anchorage and coupling with the radius bone when attached to it. For example, radial fixture 210 may be V-shaped designed to present two joined bars that are to be affixed laterally onto radial bone 165.

Radial member 155 further includes a radial articular resurfacing plate 213 having a substantially smooth concave surface that is to be located at the end of the radial bone proximal to the wrist for supporting the radial member 155 when in-situ. The wrist includes the carpal bones and multiple joints that intercommunicate in a common synovial cavity. "Proximal" to the wrist refers, in the context of the present application, to the side of radial bone 165 nearest the carpal bones. This portion of the radial bone is referred to, in the context of the present application, as the distal radius. Radial articular resurfacing plate 213 is attached substantially perpendicular to V-shaped radial fixture 210 as shown in FIG. 2.

Carpal capitate bone insert 180 includes a dorsal surface cortical plate 247 and a central intraosseous stem 249. A bulbous component 183 is configured to be flexibly coupled to carpal capitate bone insert 180 and located substantially opposite to carpal capitate bone insert 180. Bulbous component 183 includes a convex head 185 having a convex surface (e.g., the articular resurfacing plate of carpal capitate member 175).

Dorsal surface cortical plate 247 is a fixture of carpal capitate member 175 which is externally affixed to the cortical bone tissue of carpal capitate bone 125. Dorsal cortical plate 247 is maneuvered, during the implantation procedure, to be positioned on the dorsal cortical position of carpal capitate bone 125 and stem 249 is inserted into the central intraosseous position of the carpal capitate bone.

Four screw holes 220 for four screws 225 are located on both stem 249 and plate 247 of insert 180. Four screws 225 traverse carpal capitate bone 125 in the dorsal to palmar direction so as to affix plate 247 to carpal capitate bone 125 and central intraosseous stem 249; however, any number screws may be used.

The head of stem 249 includes several petals, in this example, four petals. Two petals 245 are generally oriented in the dorsal-volar direction and two petals 250 are generally oriented in the radioulnar direction. The petals are flexibly configured to snap-in, or connect to a neck 253, so as to hold bulbous component 183 to carpal capitate bone insert 180.

Radial articular resurfacing plate 213 of radial member 155 with the concave surface is configured to be operably coupled to the convex surface of convex head 185 of bulbous component 183 of carpal capitate member 175 so as to allow radial freedom of motion of bulbous component 183 of carpal capitate member 175 with respect to radial articular resurfacing plate 213 after implantation. Note that the term "operably coupled" in the context of wrist arthroplasty is defined herein to mean that in coupling, bonding, connecting or otherwise holding together the two components forming the wrist joint replacement, implant, or prostheses, with two articulating surfaces, the motion of the two articulating surfaces are identical, or most closely replicate, the same motions found in equivalent in vivo joint articulating surfaces (e.g., anatomical movements of the RCJ articulation). Stated differently by way of example, the movements, or motions, of the RCJ replacement after implantation would most closely replicate the same movements, or motions, found equivalently in a normal (healthy) radiocarpal joint in the wrist.

Radial fixture 210 (the dorsal plate), includes holes 160 through which fasteners, typically screws 225, are used for plate fixation of radial member 155 to the radial bone cortex. This technique for assembling the RCJ replacement is referred to, in the context of the present application, as dorsal radius fracture fixation. In some embodiments, holes 160 have threading for screws 225 to be fixed to radial member 155. One or more holes 227 on the central region of the "V" pass are oval shaped. Screwing screw 225 into a chosen side of oval hole 227 applies a longitudinal stress to fixture 210 in the direction of the chosen side so as to allow an additional degree of freedom for placing and fastening radial fixture 210 to radius bone 215. Although a V-shaped radial fixture is described, aimed at providing good mechanical stability, other shapes may be considered, too. The V-shape is not in any way limiting the embodiments of the present invention to that shape. Other shapes for the radial fixture may be used with varying number of screws and respective screw holes in any geometric orientation.

Radial fixture 210 (dorsal plate) is also connected to radial articular resurfacing plate 213. Two triangular pegs 230 that are formed in the bottom side of radial articular resurfacing plate 213 are designed to be pressed against and penetrate into the end of the radius bone as shown in FIG. 2, for enhanced stability. Triangular pegs 230 also include holes 240. Screws 235 may be screwed through obliquely threaded screw holes 234 formed in radial fixture 210 (e.g., dorsal plate). Screw holes 234 are not on the same lateral position along both side of fixture 210 so as to compensate for the shapes of radial bone 165 and the end of radial bone 165 (e.g., the radial articular surface). Screws 235 pass through radius bone 165 to threaded screw holes 235 and 240 at an oblique angle of about 43 degrees with the bottom surface of radial articular resurfacing plate 213 opposite radius bone 165. Fastening screws 235 are used for affixing radial member 155 via pegs 230 of the radiocarpal joint (RCJ) replacement to radial bone 165, which forms a mechanically stable pyramid-like closed frame, enhancing self-support.

Figures 3A, 3B, 3C, 3D, 3E, 3F:
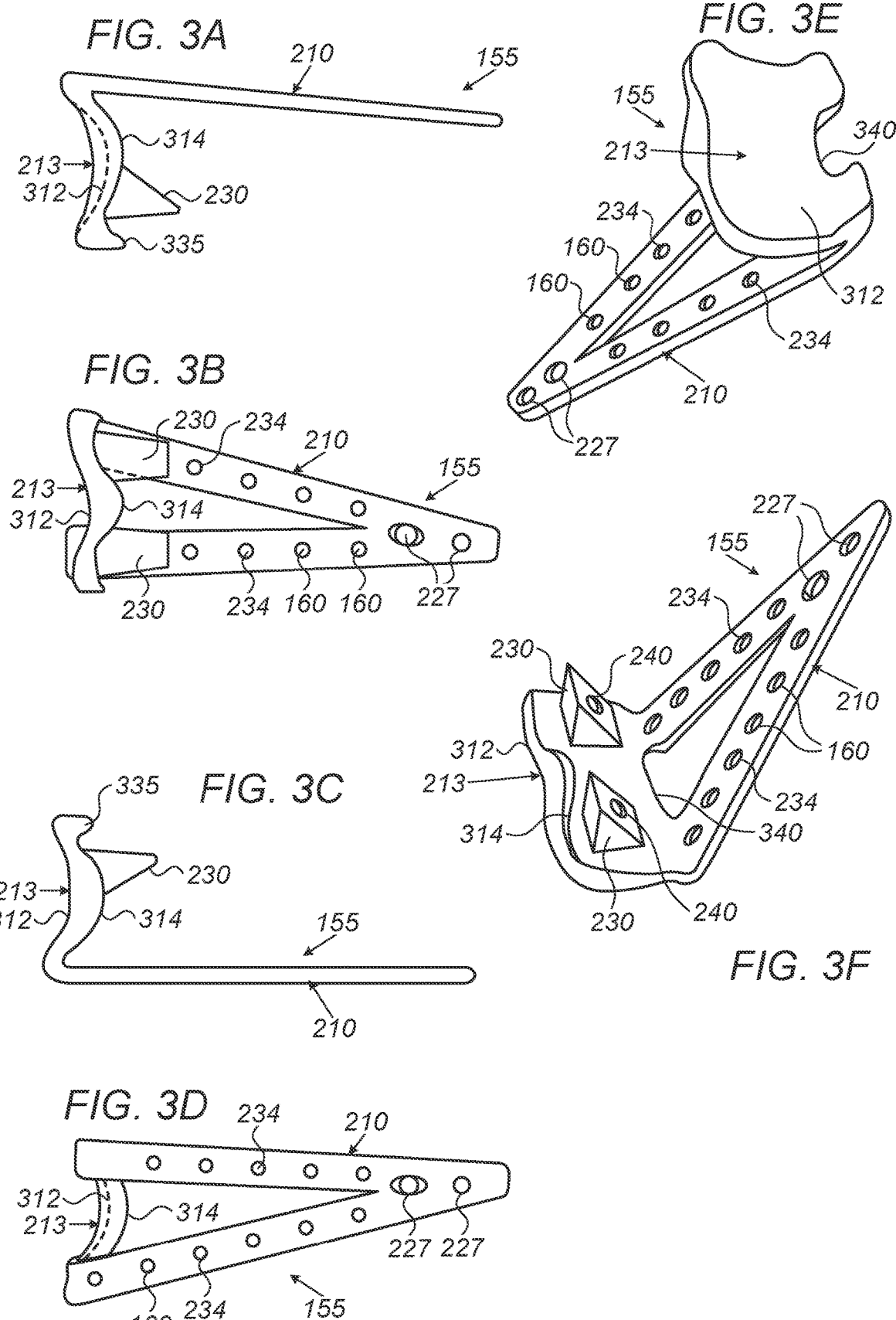
FIG. 3A schematically illustrates a first side view of a radial member, in accordance with some embodiments of the present invention.
FIG. 3B schematically illustrates a bottom view of a radial member, in accordance with some embodiments of the present invention.
FIG. 3C schematically illustrates a second side view of a radial member, in accordance with some embodiments of the present invention.
FIG. 3D schematically illustrates a top view of a radial member, in accordance with some embodiments of the present invention.
FIG. 3E schematically illustrates a first perspective view of a radial member, in accordance with some embodiments of the present invention.
FIG. 3F schematically illustrates a second perspective view of radial member, in accordance with some embodiments of the present invention.

FIG. 3A schematically illustrates a first side view of radial member 155, in accordance with some embodiments of the present invention.

FIG. 3B schematically illustrates a bottom view of radial member 155, in accordance with some embodiments of the present invention.

FIG. 3C schematically illustrates a second side view of radial member 155, in accordance with some embodiments of the present invention.

FIG. 3D schematically illustrates a top view of radial member 155, in accordance with some embodiments of the present invention.

FIG. 3E schematically illustrates a first perspective view of radial member 155, in accordance with some embodiments of the present invention.

FIG. 3F schematically illustrates a second perspective view of radial member 155, in accordance with some embodiments of the present invention.

Radial member 155 of the radiocarpal joint (RCJ) replacement includes a radial fixture 210 which is integrally formed with radial articular resurfacing plate 213. Radial articular resurfacing plate 213 is concave 312 toward the carpus, or carpal bones, and convex surface 314 toward the radial articular surface of the radial bone according to the normal anatomical concavity of the articular surface of the distal radius. In some embodiments, radial articular resurfacing plate 213 with concave surface 312 is fabricated or formed to present a highly polished metal surface. Convex surface 314 may be coated (e.g., hydroxylapatite) for better contact with the distal radius bone and also to allow for bone growth.

Radial fixture 210 also includes holes 160 for screws to affix the radial member 155 to the cortex of the radius and an oval hole 227 which allows another longitudinal degree of freedom in firmly attaching radial fixture 210 to the radius bone as described in FIG. 2. The volar ridge of plate 213 (e.g., side of plate 213 proximal to the palm of the subject's hand) includes a volar hook 335. Volar hook 335 increases the stability of radial articular resurfacing plate 310 mounted on to the end of the radius bone proximal to the wrist.

Two triangular pegs 230 are formed in convex surface 314 of radial articular resurfacing plate 213 (e.g., on the volar portion of plate 213). Pegs 230 have screw holes 240 such that two lock screws 235 mounted through holes 240 and holes 234 (as described in FIG. 2) formed in radial fixture 210 prevent a rotation of radial articular resurfacing plate 213. Radial articular resurfacing plate 213 has a deltoid notch 340 so as to accommodate Lister's tubercle and the bone joint capsule.

Figure 4A:
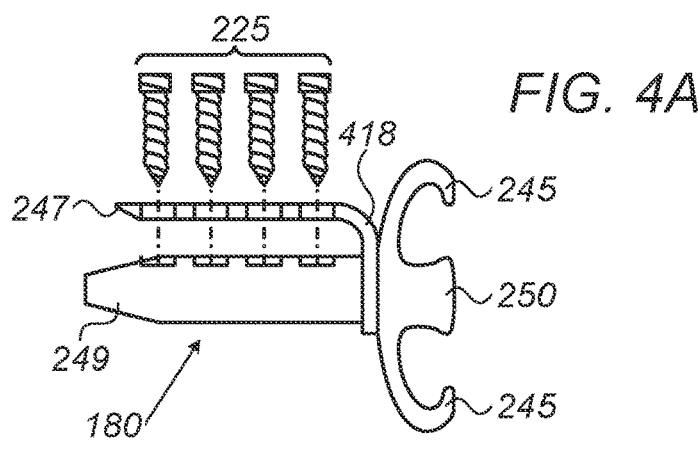
FIG. 4A schematically illustrates a side view of a carpal capitate bone insert, in accordance with some embodiments of the present invention.

FIG. 4A schematically illustrates a side view of carpal capitate bone insert 180, in accordance with some embodiments of the present invention. When implanting carpal capitate bone insert 180, central intraosseous stem 249 is inserted and implanted into the central intraosseous position of the carpal capitate bone. Dorsal cortical plate 247 is maneuvered, during the implantation procedure, to be positioned on the dorsal cortical position of carpal capitate bone 125.

Four screw holes 220 for four screws 225 are located on both stem 249 and plate 247 of insert 180. Four screws 225 traverse and are threaded through carpal capitate bone 125 in the dorsal to palmar direction so as to affix plate 247 to carpal capitate bone 125 and central intraosseous stem 249; however, any number screws may be used. Holes 220 in plate 247 are parallel to holes 220 in stem 249. Plate 247 is connected to stem 249 at a proximal end 418 of stem 249. Also connected to a proximal end 418 of stem 249 are four petals. Two petals 245 are oriented in the dorsal-volar direction and two petals 250 are oriented in the radioulnar direction.

In some embodiments, carpal capitate bone insert 180 may be formed from titanium or stainless steel. In other embodiments, stem 249 are prepared with plasma deposited hydroxylapatite which gives stem 249 a corrugated coated surface for better bone growth and adhesion when stem 249 is implanted within the central intraosseous position of the carpal capitate bone.

Figure 4B:
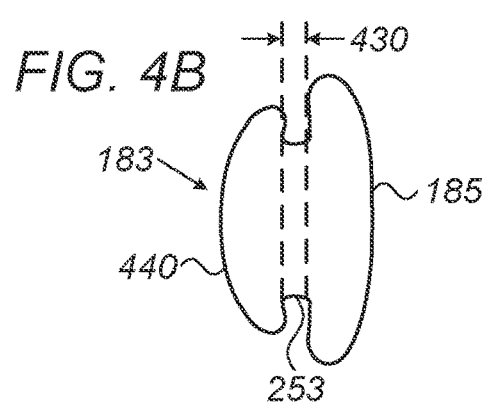
FIG. 4B schematically illustrates a side view of a bulbous component, in accordance with some embodiments of the present invention.

FIG. 4B schematically illustrates a side view of bulbous component 183, in accordance with some embodiments of the present invention. Bulbous component 183 includes a first convex head 440 and (second) convex head 185 (as described previously in FIGS. 1-2), substantially opposite each other and connected by neck 253 defining an annular groove 430 between first convex head 440 and second convex head 185.

Figure 4C:
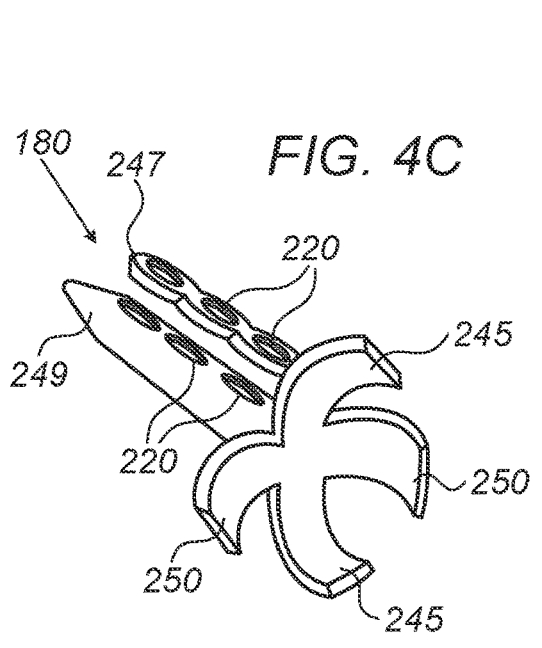
FIG. 4C schematically illustrates a perspective view of a carpal capitate bone insert, in accordance with some embodiments of the present invention.

FIG. 4C schematically illustrates a perspective view of carpal capitate bone insert 180, in accordance with some embodiments of the present invention.

Figure 4D:
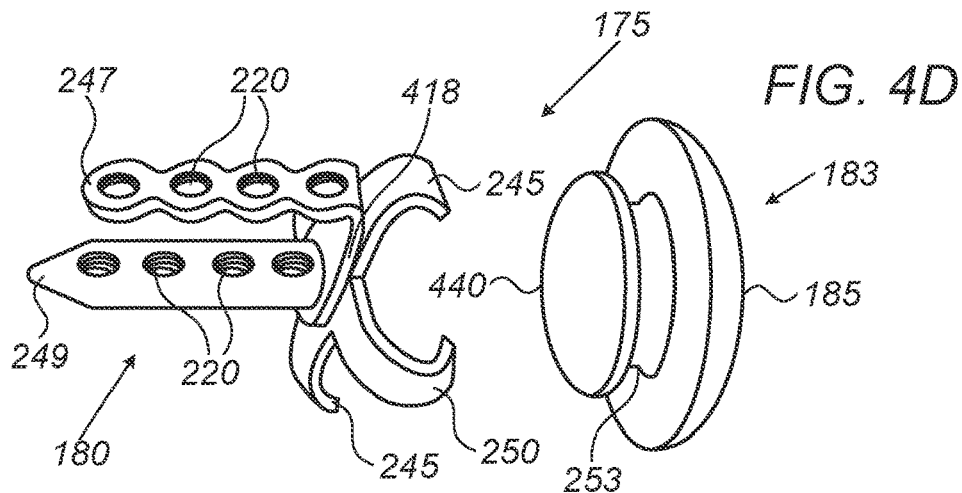
FIG. 4D schematically illustrates a top view of a carpal capitate bone insert and a bulbous component, in accordance with some embodiments of the present invention.

FIG. 4D schematically illustrates a top view of carpal capitate bone insert 180 and bulbous component 183, in accordance with some embodiments of the present invention. The four petals are substantially flexible and are configured to snap into annular ring 430 of neck 253 of bulbous component 183. Thus, the petals squeeze, hold, or bite on neck 253 of the bulbous component under pressure, which affixes carpal capitate bone insert 180 to bulbous component 183. However since the petals are flexible, small deviations in motion up to 4 mm in any direction between central intraosseous stem 249 and first convex head 440 of bulbous component 183 may occur. Thus, in this context of the present application, the carpal capitate bone insert 180 is configured to be flexibly coupled to first convex head 440 of the bulbous component. A carpal capitate member may be defined herein as to include carpal capitate bone insert 180 flexibly coupled to bulbous component 183.

According to some embodiments of the invention, there may be provided bulbous components with different neck sizes to cater for various palm sizes. Bulbous component 183 may be made from a material selected from the group consisting of polyethylene, pyrocarbon, and ceramic. Similarly, the bulbous components may be provided with second convex heads 185 of different sizes. However, the size of second convex heads 185 is typically the same or similar for most purposes. The size of the carpal capitate member and can be predetermined by snapping in a bulbous component, for example, having the proper neck size to suit the patient's palm size. The adjustment of the size of the carpal capitate member in this manner can be used to balance between the tension and wrist motion during implantation so as optimize performance of the RCJ replacement.

The RCJ replacement effectively has two joints that can move during the motion of the RCJ wrist replacement. Movement in the first joint in the RCJ replacement mainly occurs where the convex surface of second convex head 185 is configured to be operably coupled to radial articular resurfacing plate 213. The area of the convex head articulates with the radial articular resurfacing plate of substantially the same area. In addition, the flexible coupling between carpal capitate bone insert 180 and bulbous component 183 forms a second flexible joint with another degree of freedom in the movement of the overall RCJ replacement.

The flexible movements possible in the second joint are small relative to the large radial movements in the first joint.

Figure 5:
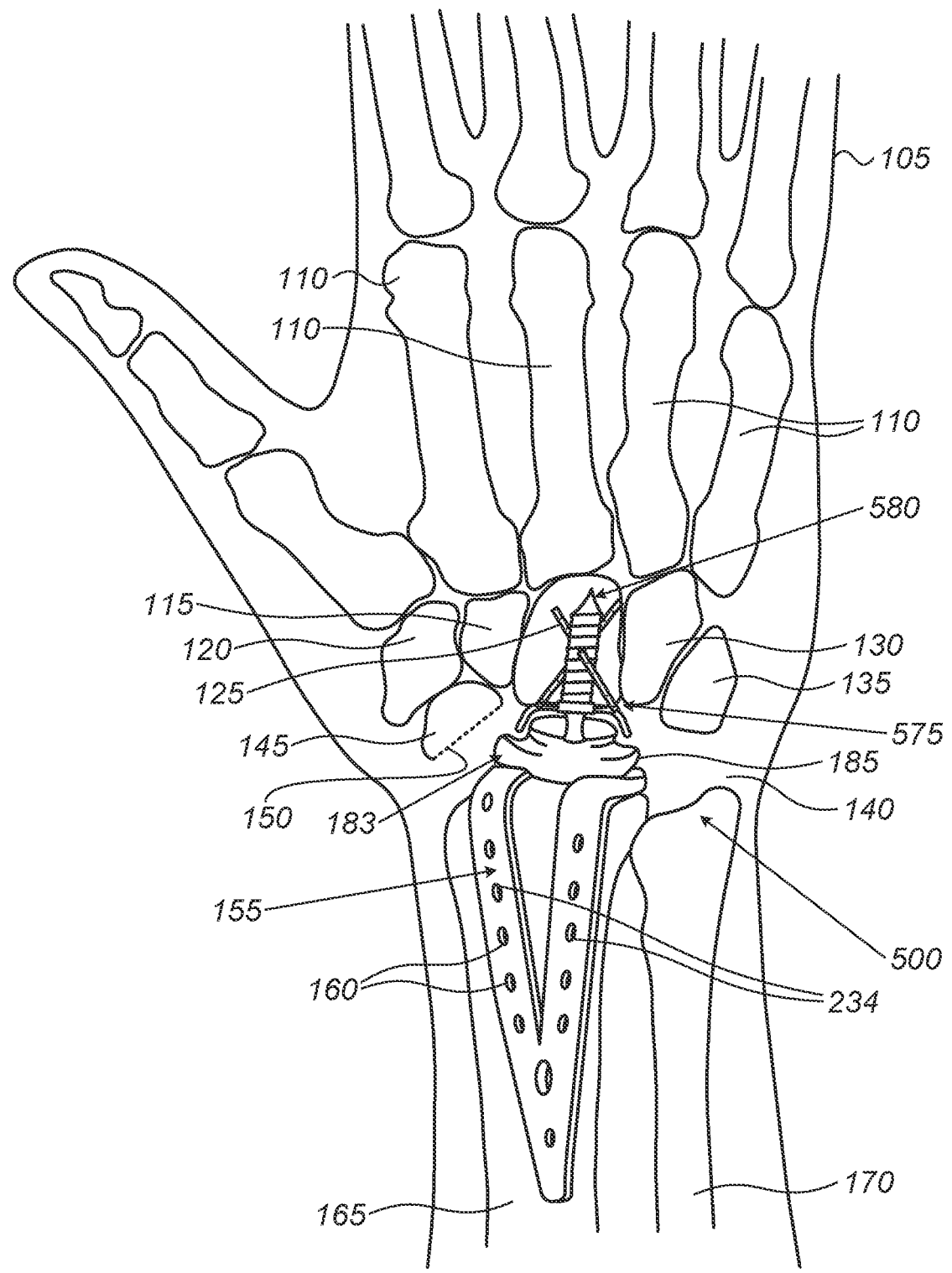
FIG. 5 schematically illustrates a dorsal view of a hand with a radiocarpal joint (RCJ) replacement, in accordance with some embodiments of the present invention.

FIG. 5 schematically illustrates a dorsal view of hand 105 with radiocarpal joint (RCJ) replacement 500, in accordance with some embodiments of the present invention. Dorsal view 500 of hand 105 includes metacarpal bones 110, and the carpal bones, or carpus, including carpal trapezoid bone 115, carpal trapezium bone 120, carpal capitate bone 125, carpal hamate bone 130, and carpals triquetral/pisiform bones 135.

To implant the RCJ replacement in the second embodiment of FIG. 5 in the wrist of hand 105, the carpal lunate bone is removed from a region 140 from hand 105. A carpal scaphoid bone 145 is surgically cut along a cut plane 150 and cartilage is removed from the RCJ. Radius bone 165 and ulna bone 170 are shown in FIG. 5.

A radial member 155 of the RCJ replacement includes radial member holes 160 through which fasteners, typically screws can be inserted and threaded to allow affixing or locking radial member 155 to a portion of an end of radius bone 165 proximal to the wrist. In contrast to soft tissue mounting of implants, radial member 155 is typically affixed to the cortex of radius bone 165 to provide a solid mechanical support for the RCJ replacement.

A carpal capitate member 575 includes a carpal capitate insert screw 580 and bulbous head 183. Carpal capitate member 575 of the RCJ replacement is configured to be affixed by screw 580 only to carpal capitate bone 125 of the wrist, but not to other carpal bones, allowing greater maneuverability of the wrist, as a result. Screw 580 may also be referred to as a carpal capitate member fixture of carpal capitate member 575 held externally affixed by the cortical bone tissue and enters the cancellous bone tissue inside. The head of screw 580 includes a spherical highly polished small head. In the same manner, as described in FIG. 4, carpal capitate insert screw 580 is flexibly coupled to bulbous component 183 with convex head 185.

Figure 6:
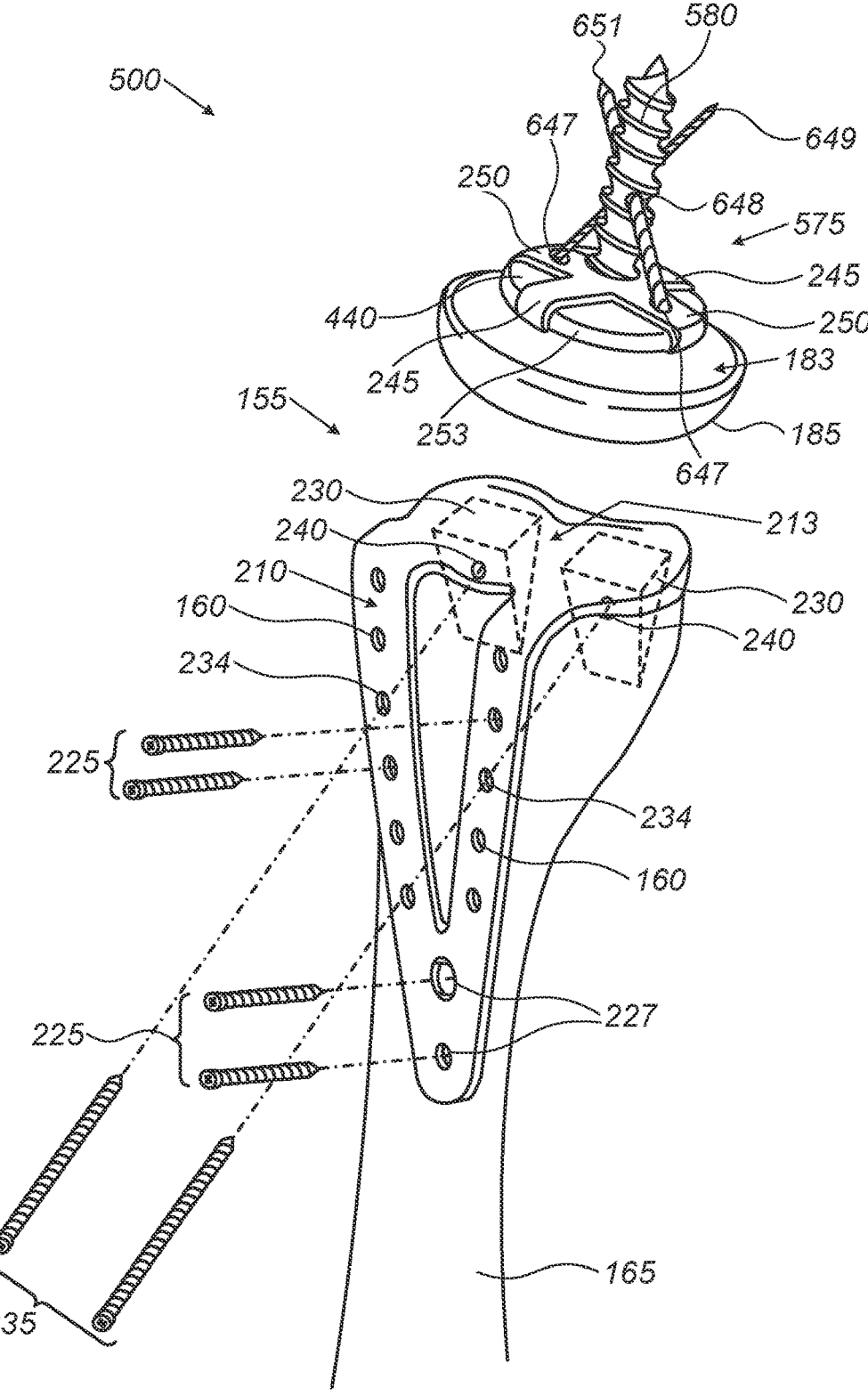
FIG. 6 schematically illustrates an exploded view of a radiocarpal joint (RCJ) replacement, in accordance with some embodiments of the present invention.

FIG. 6 schematically illustrates an exploded view 600 of a radiocarpal joint (RCJ) replacement, in accordance with some embodiments of the present invention. A radial member 155 of the radiocarpal joint (RCJ) replacement includes a radial fixture 210 in the shape of a "V" which affixed the radial member laterally onto radial bone 165 and radial articular resurfacing plate 213 having a substantially smooth concave surface located at the end of the radial bone proximal to the wrist. Radial articular resurfacing plate 213 is attached at a nearly 90 degree angle to V-shaped radial fixture 210 as shown in FIG. 6.

Carpal capitate member 575 includes screw 580 with wide threads along the shank which is inserted, threaded, implanted, or affixed to the carpal capitate bone. The head of screw 580 includes four petals. Two petals 245 are oriented in the dorsal-volar direction and two petals 250 are oriented in the radioulnar direction. The petals are configured to be connected to a neck 253 of bulbous component 183. Two petals 250 oriented in the radioulnar direction each have threaded oblique holes 647.

After implantation of the screw into the carpal capitate bone, two locking screws are threaded through the carpal capitate bone, through channels 648 formed in the shank of main capitate screw 580 and into oblique holes 647. A first locking screw 649 is mounted from threaded oblique hole 647 and is oriented toward the ulnar dorsal base of the carpal capitate bone. A second locking screw 651 is mounted from threaded oblique hole 647 and is oriented toward the radial volar base of the carpal capitate bone. The shank of screw 580 is coated for good contact and good bone growth with plasma deposited hydroxylapatite for implantation within the central intraosseous position of the carpal capitate bone.

Stated differently, in some embodiments, carpal capitate insert includes an implant insertion element selected from the group consisting of stem 249 and screw 580. The implant insertion element is implanted into the central intraosseous position of the carpal capitate bone and may be coated with hydroxylapatite.

Bulbous component 183 includes a convex head 185 having a convex surface. The four petals 245 and 250 are substantially flexible and allow the insertion of bulbous component 183 such that the four petals squeeze and bite down on annular ring 430 of neck 253 as described in FIG. 4 so as to affix the bulbous component to the carpal capitate bone insert. Applying bulbous components with different neck sizes, for example, allow for adjusting the size of carpal capitate member (e.g., bone insert 575 and bulbous component 183) as described for the embodiment shown in FIG. 4 so as to balance between the tension and wrist motion during implantation.

Radial articular resurfacing plate 213 of radial member 155 with the concave surface is configured to be operably coupled to the convex surface of convex head 185 of bulbous component 183 of carpal capitate member 575 so as to allow radial freedom of motion of bulbous component 183 of carpal capitate member 575 with respect to radial articular resurfacing plate 213 after implantation. The area of the convex surface of convex head 185 is substantially the same as the area of radial articular resurfacing plate 213.

Radial fixture 210, or dorsal plate, includes holes 160 through which fasteners, typically screws 225, are used for plate fixation of radial member 155 to the radial bone cortex. This technique for assembling the RCJ replacement may also be referred to as dorsal radius fracture fixation. In some embodiments, holes 160 have threading for screws 225 to be fixed to radial member 155. Two or three holes 227 on the central region of the "V" are oval which allow compression of radial fixture 210 longitudinally to radius bone 165.

Radial fixture 210 (dorsal plate) is also connected to radial articular resurfacing plate 213. Two triangular pegs 230 that are formed in the bottom side of radial articular resurfacing plate 213 are designed to be pressed against and penetrate into the end of the radius bone as shown in FIG. 2, for enhanced stability. Triangular pegs 230 also include holes 240. Screws 235 may be screwed through obliquely threaded screw holes 234 formed in radial fixture 210 (e.g., dorsal plate). Screw holes 234 are not on the same position along fixture 210 so as to compensate for the shapes of radial bone 165 and the end of radial bone 165 (e.g., the radial articular surface). Screws 235 pass through radius bone 165 to threaded screw holes 240 at an oblique angle of about 43 degrees with the bottom surface of radial articular resurfacing plate 213 opposite radius bone 165. Fastening screws 235 are used for affixing radial member 155 via pegs 230 of the radiocarpal joint (RCJ) replacement to radial bone 165, which forms a mechanically stable pyramid-like closed frame, enhancing self-support.

Figure 7:
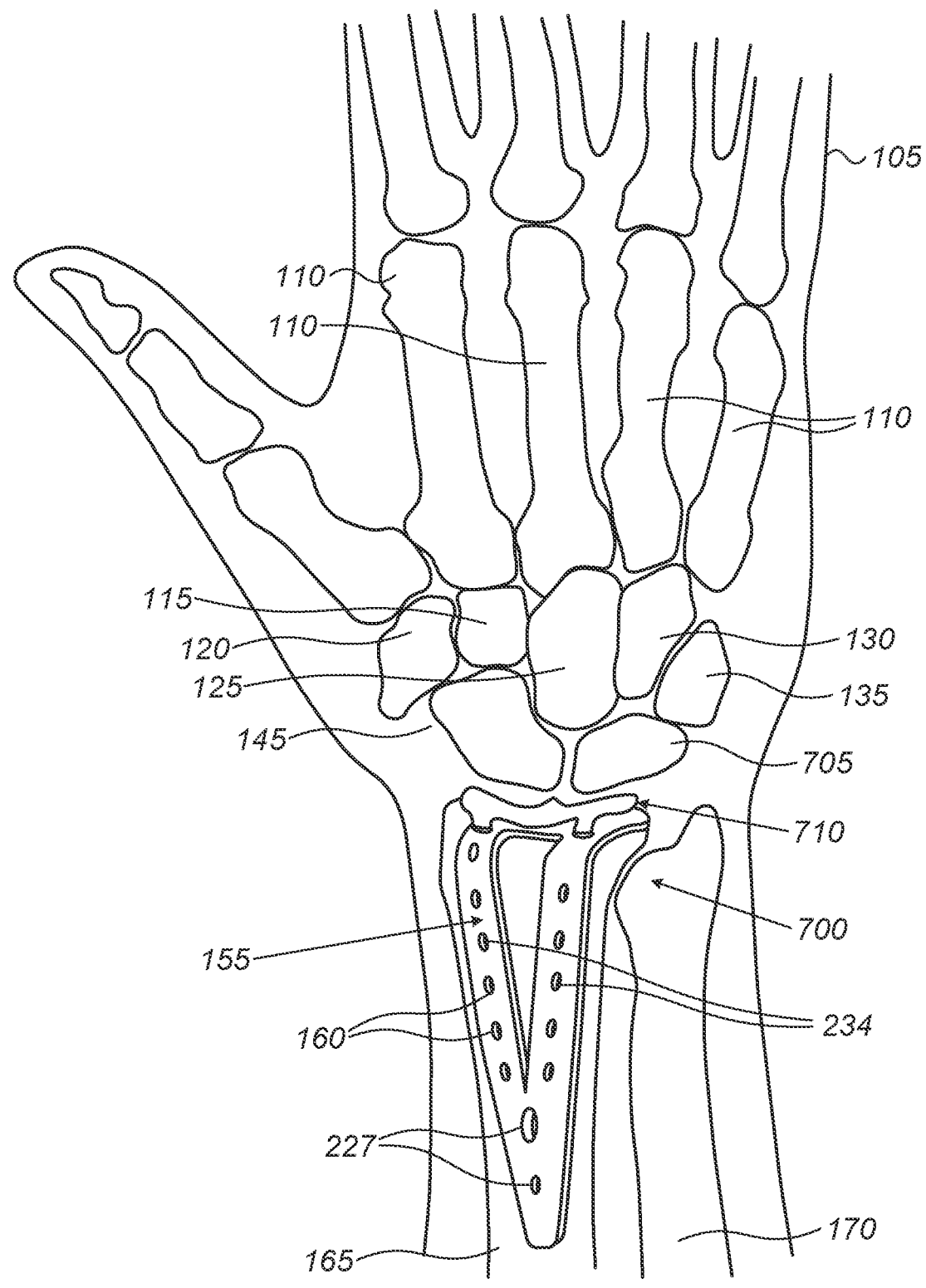
FIG. 7 schematically illustrates a dorsal view of a hand with a radiocarpal joint (RCJ) cartilage replacement, in accordance with some embodiments of the present invention.

FIG. 7 schematically illustrates a dorsal view of hand 105 with a radiocarpal joint (RCJ) cartilage replacement 700, in accordance with some embodiments of the present invention. The wrist bones shown in FIG. 7 are identical to that of FIG. 1 with the exception that carpal scaphoid bone 145 is not surgically cut and the carpal lunate bone 705 is not removed as described previously for the RCJ joint replacement. Here, all of the carpal bones are present. In the event of a sports injury where cartilage in the RCJ joint is fractured or damaged, the damaged cartilage is removed. However, a plastic cartilage replacement 710 is inserted and attached to radial member 155. The carpal bones are operably coupled to cartilage replacement 710 on a first side proximal to the wrist (e.g., to the carpal bones) so as to restore normal wrist motion after the RCJ cartilage was removed. The second side of cartilage replacement 710 is affixed to radial member 155.

Figure 8:
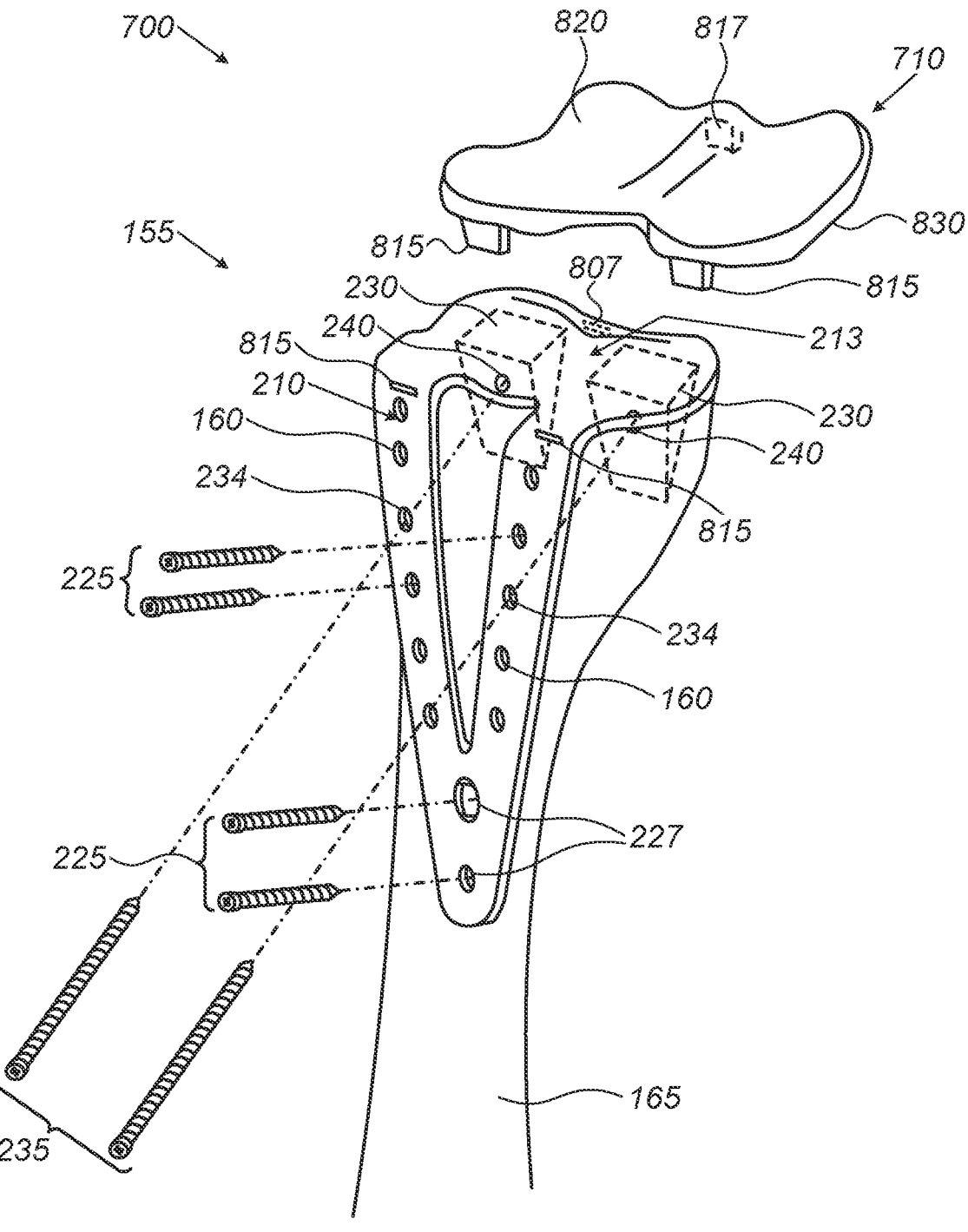
FIG. 8 schematically illustrates an exploded view of a radiocarpal joint (RCJ) cartilage replacement, in accordance with some embodiments of the present invention.

FIG. 8 schematically illustrates an exploded view of radiocarpal joint (RCJ) cartilage replacement 700, in accordance with some embodiments of the present invention. Radial member 155 is affixed to a portion of an end of radial bone 165 proximal to the wrist (e.g., the carpal bones of the wrist) by the same procedures described in the embodiments shown in FIGS. 1-6. However, radial member 155 also includes tab holes 805 and 807 which are configured to receive tabs 815 and 817 respectively that are formed on side 830 of cartilage replacement 710 proximal to radial member 155. In this manner, second side 830 of cartilage replacement 710 is affixed to radial member 155. Along a first side 820 of cartilage replacement 710, the carpal bones are operably coupled to of cartilage replacement 710, such that the wrist with cartilage replacement 710 can substantially exhibit the same motions as a normal (healthy) wrist.

Figure 9A:
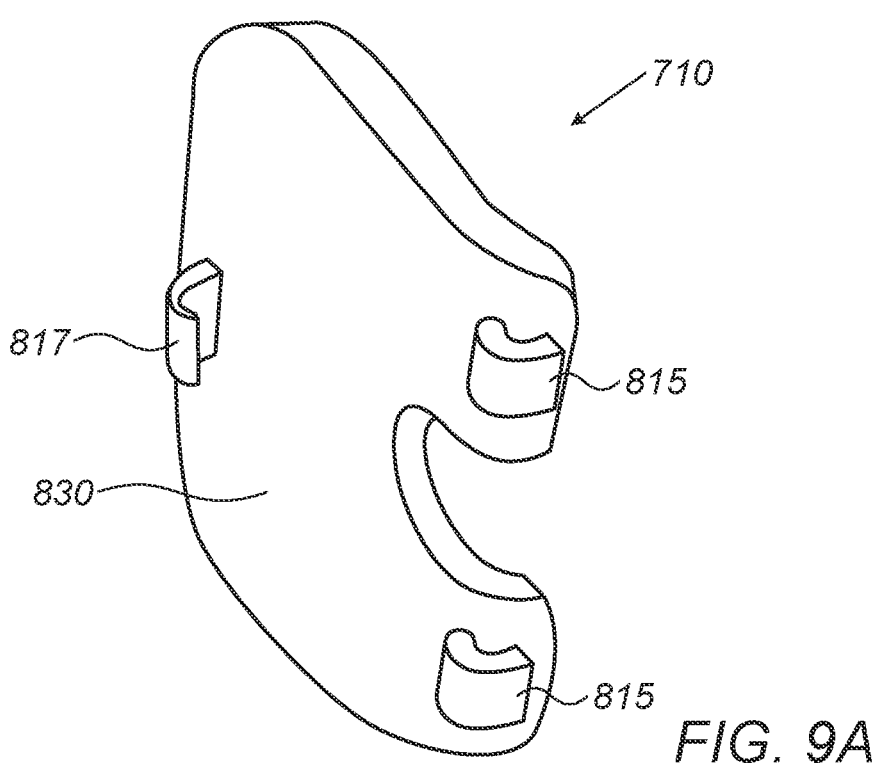
FIG. 9A schematically illustrates a bottom view of a cartilage replacement, in accordance with some embodiments of the present invention.

FIG. 9A schematically illustrates a bottom view of cartilage replacement 710, in accordance with some embodiments of the present invention. The bottom view of cartilage replacement 710 shows tabs 815 and 817 formed in side 830 (e.g., the second side affixed to radial member 155).

Figure 9B:
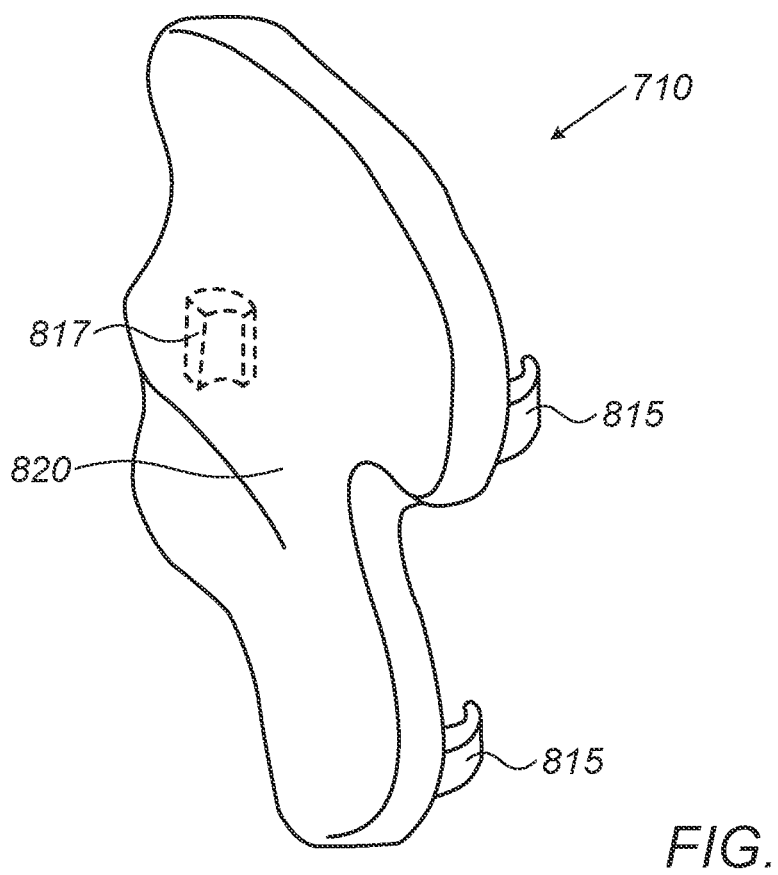
FIG. 9B schematically illustrates a top view of a cartilage replacement, in accordance with some embodiments of the present invention.

FIG. 9B schematically illustrates a top view of cartilage replacement 710, in accordance with some embodiments of the present invention. The top view of cartilage replacement 710 shows concave surface 820 (e.g., the first surface). In some embodiments, the plastic of concave surface 820 is machined and polished with optimal concavity to be operably coupled to the carpal bones in the wrist, such as for example, optimized to articulate with carpal scaphoid 145 and carpal lunate 705 (see FIG. 7).

When pathologies exist in the distal radioulnar joint (DRUJ), such as sigmoid notch damage, that affect supination and pronation movements of the wrist, a DRUJ replacement can be implanted to alleviate the dysfunction.

Figure 10:
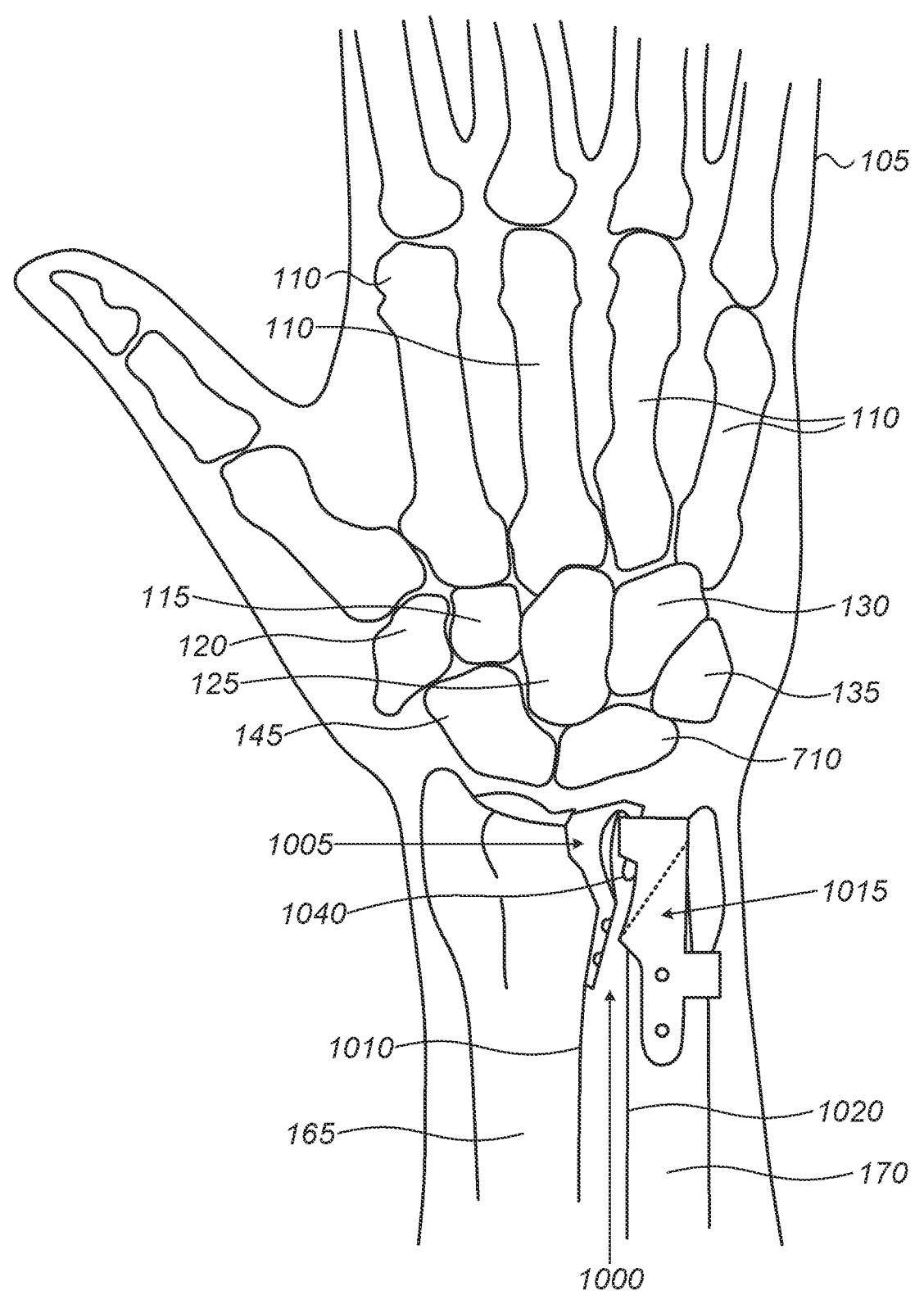
FIG. 10 illustrates a dorsal view of a hand with a distal radioulnar joint (DRUJ) replacement, in accordance with some embodiments of the present invention.

FIG. 10 illustrates a first dorsal view of hand 105 with a distal radioulnar joint (DRUJ) replacement 1000, in accordance with some embodiments of the present invention. A sigmoidal member 1005 is affixed to an ulnar side 1010 of radius bone 165 proximal to the wrist, or the bones in the wrist. An ulnar member 1015 is affixed to a radial side 1020 of ulna bone 170 and proximal to the wrist bones. Sigmoidal member 1005 also includes a hook 1040 which is inserted and held in ulnar member 1015 such that sigmoidal member 1005 is configured to be operably coupled to ulnar member 1015 so as to facilitate supination and pronation movement of the wrist and provide DRUJ stability.

Figure 11:
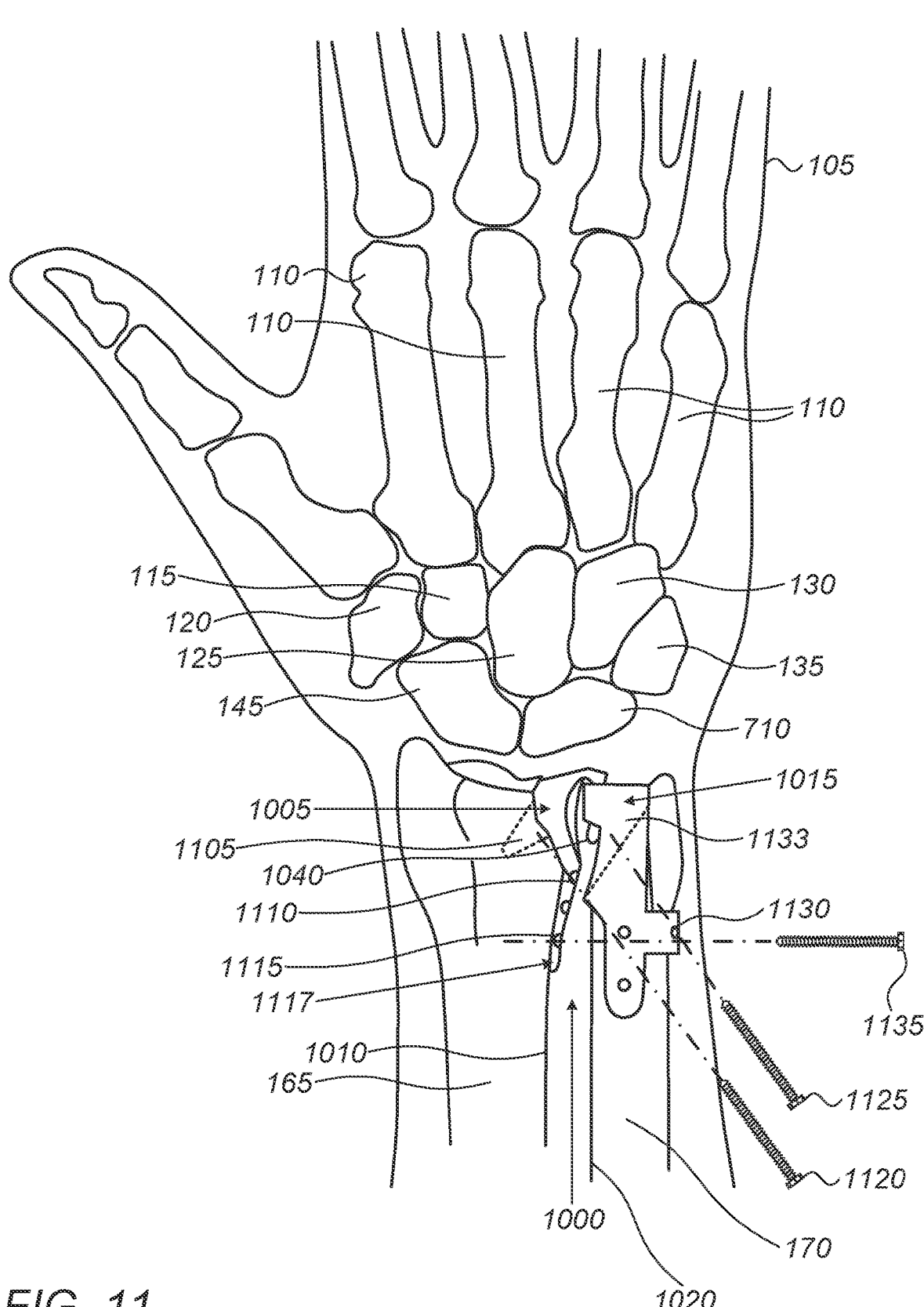
FIG. 11 schematically illustrates a dorsal view of a hand with a distal radioulnar joint (DRUJ) replacement, in accordance with some embodiments of the present invention, showing the direction of applying screws in fixing the DRUJ in position.

FIG. 11 schematically illustrates a second dorsal view of hand 105 with distal radioulnar joint (DRUJ) replacement 1000, in accordance with some embodiments of the present invention. Sigmoidal member 1005 includes a triangular peg 1105 that includes a threaded hole (not shown). Triangular peg 1105 is impacted, implanted, pressed, or hammered into the cancellous bone of the distal radius. Sigmoidal member 1005 is affixed to the distal radius by a screw 1120 that is inserted into a screw hole 1110 and is threaded into a screw hole (not shown) in triangular peg 1105. Similarly, a lower mounting bracket 1117 of sigmoidal member 1005 is affixed to radius bone 165 along ulnar side 1010 by a screw 1135 which is threaded into a screw hole 1115. Lower mounting bracket 1117 is affixed over a longitudinal aspect of the radial bone. This closed frame construction provides stability and dissipates forces across sigmoidal member 1005, which is similar to the topology for affixing radial member 155.

Ulnar member 1015 is also constructed with a triangular block 1133 that restores a partial oblique resection of the articular surface of an ulnar head 1140 of ulna bone 170, restoring nearly ⅔ of the ulnar head. Ulnar member 1015 is partially affixed by a screw 1125 inserted to threaded through screw hole 1130 into triangular block 1133.

Figure 12:
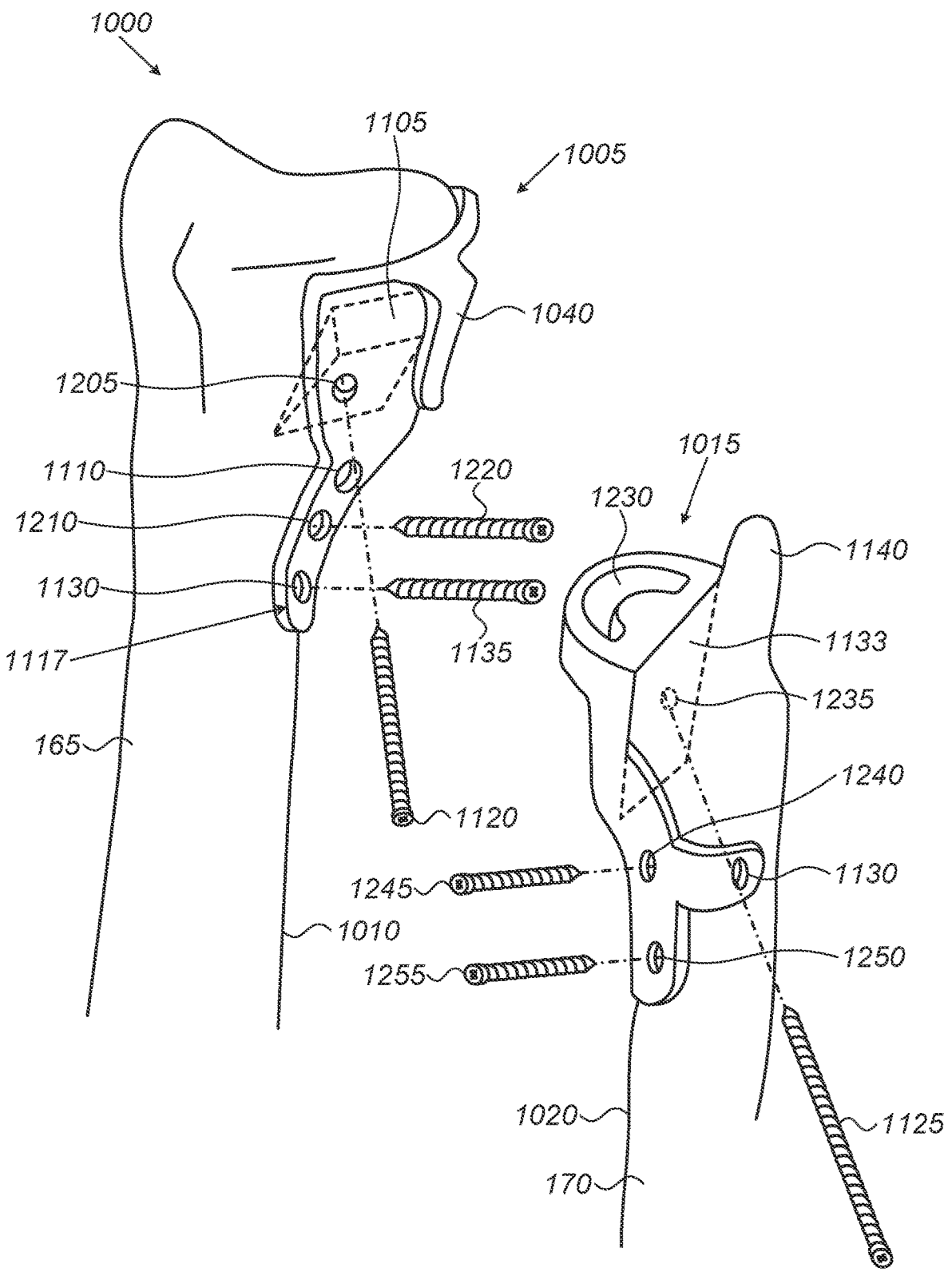
FIG. 12 schematically illustrates an exploded view of a distal radioulnar joint (DRUJ) replacement, in accordance with some embodiments of the present invention.

FIG. 12 schematically illustrates an exploded view of distal radioulnar joint (DRUJ) replacement 1000, in accordance with some embodiments of the present invention. Sigmoidal member 1005 includes hook 1040. After impacting peg 1105 into the distal radius bone as described previously, sigmoidal member 1005 is affixed to the radius bone 165 by three screws. Screw 1120 is threaded obliquely through hole 1110 through the radial head into a threaded hole 1205 in peg 1105. Lower mounting bracket 1117 of sigmoidal member 1005 is affixed to radius bone 165 along ulnar side 1010 by screw 1135 threaded into screw hole 1115, and a screw 1220 threaded into a screw hole 1210.

A bore 1230 is formed into ulnar portion 1015. Bore 1230 may also be referred to herein as a supination-pronation tunnel. In some embodiments, bore 1230 may include a track formed in ulnar portion 1015. In other embodiments, bore 1230 may include a groove formed in ulnar portion 1015. Ulnar portion 1015 is held to ulna bone 170 by three screws as shown in FIG. 12. Screw 1125 is inserted obliquely into threaded hole 1130 crosses the resected portion of the ulna head and is threaded into a hole 1235 in triangular block 1133. The lower portion of the ulnar member is affixed to ulna bone 170 by two screws 1245 and 1255 in threaded screw holes 1240 and 1250, respectively. Threaded screw holes 1240 and 1250 may also have oval holes which can be provide axial compress of the ulnar member along the ulna bone.

Hook 1040 of sigmoidal member 1005 is inserted and held in bore 1230 in ulnar member 1015 which is configured to receive hook 1040, and retain the hook after implantation. Although bore 1230 is shaped like a "C", the C-shape has been determined to provide good stability of the DRUJ replacement when the wrist is moved in pronation and supination, any suitable bore shape can be chosen so as to optimize the joint stability and performance.

Figure 13A:
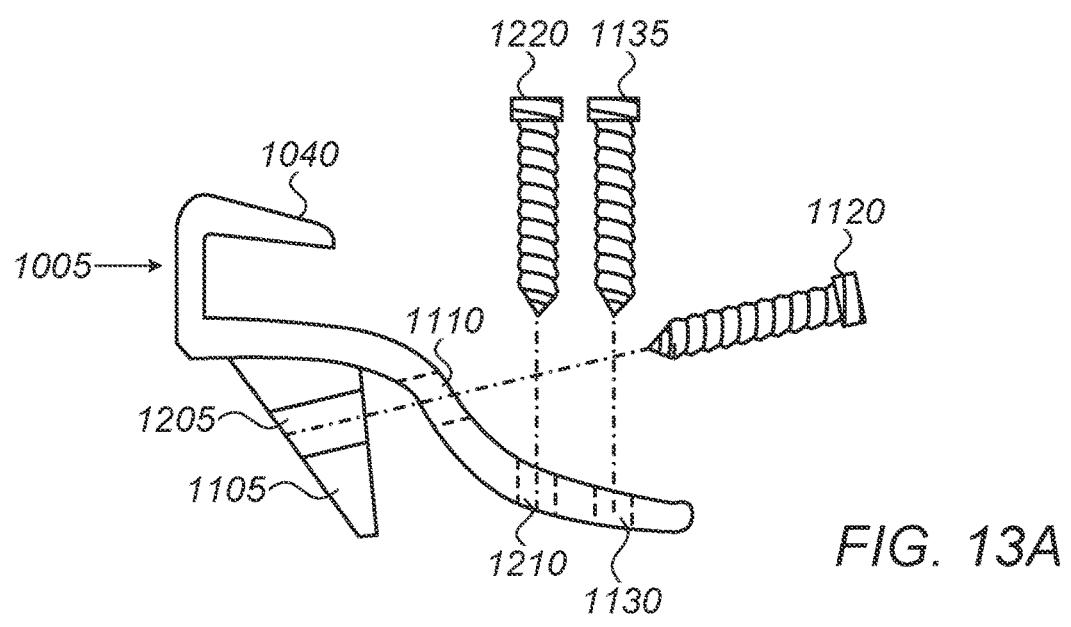
FIG. 13A schematically illustrates a side view of a sigmoidal member with a hook, in accordance with some embodiments of the present invention.

FIG. 13A schematically illustrates a side view of sigmoidal member 1005 with hook 1040, in accordance with some embodiments of the present invention.

Figure 13B:
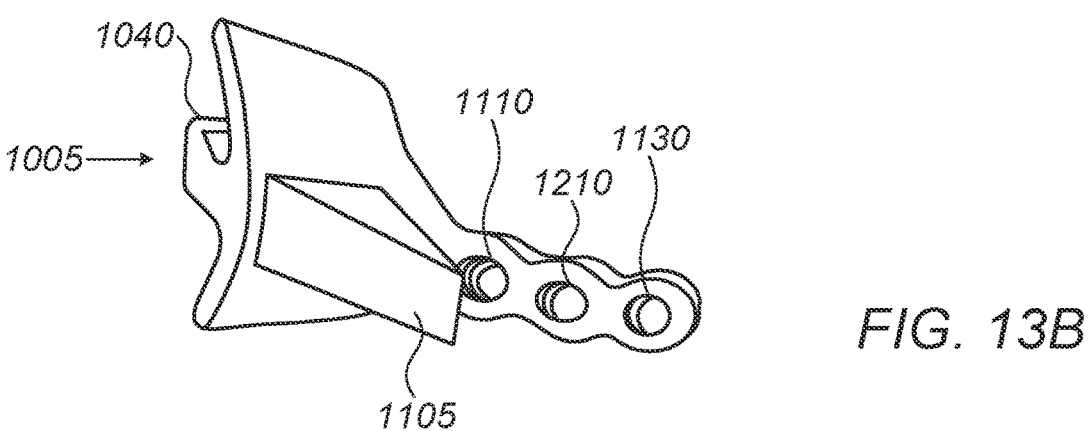
FIG. 13B schematically illustrates a top view of a sigmoidal member with a hook, in accordance with some embodiments of the present invention.

FIG. 13B schematically illustrates a top view of sigmoidal member 1005 with hook 1040, in accordance with some embodiments of the present invention.

Figure 13C:
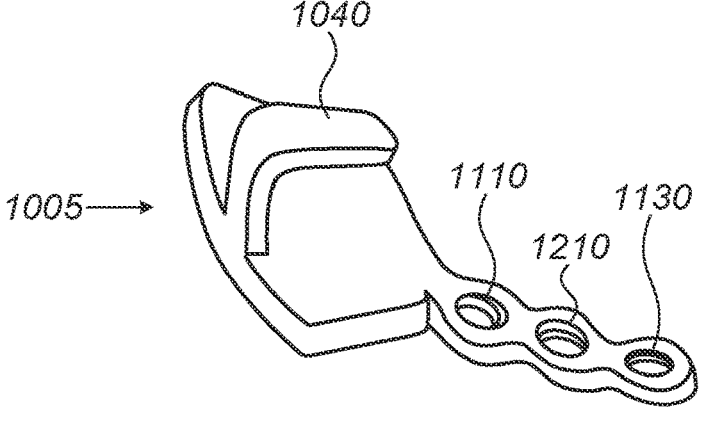
FIG. 13C schematically illustrates a bottom view of a sigmoidal member with a hook, in accordance with some embodiments of the present invention.

FIG. 13C schematically illustrates a bottom view of sigmoidal member 1005 with hook 1040, in accordance with some embodiments of the present invention.

Peg 1105 is impacted into the cancellous bone of the distal radius and affix to radius 165 by screw 1120 threaded through holes 1110 and 1205. The screws and screw holes are the same as described in FIGS. 10-12. Sigmoidal member 1005 may be formed from polished stainless steel or titanium.

Figures 14A, 14B, 14C:
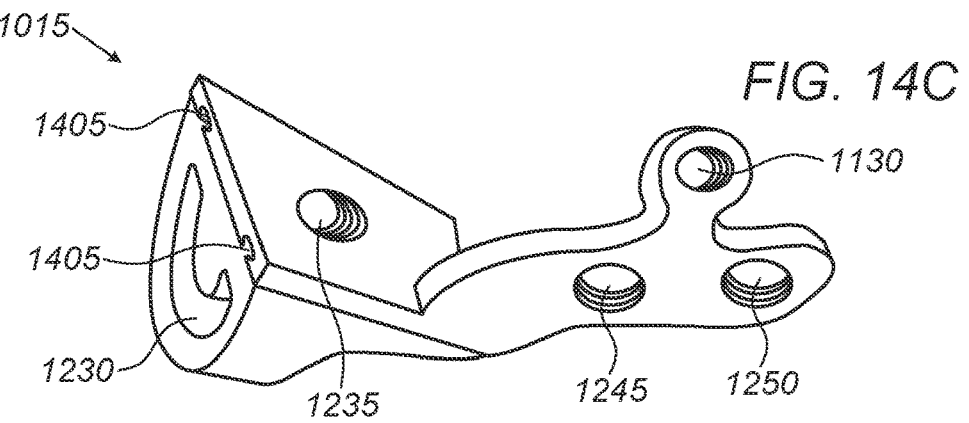
FIG. 14A schematically illustrates an exploded view of an ulnar member with a bore, in accordance with some embodiments of the present invention.
FIG. 14B schematically illustrates a first perspective view of an ulnar member with a bore, in accordance with some embodiments of the present invention.
FIG. 14C schematically illustrates a second perspective view of an ulnar member with a bore, in accordance with some embodiments of the present invention.

FIG. 14A schematically illustrates an exploded view of ulnar member 1015 with bore 1230, in accordance with some embodiments of the present invention.

FIG. 14B schematically illustrates a first perspective view of ulnar member 1015 with bore 1230, in accordance with some embodiments of the present invention.

FIG. 14C schematically illustrates a second perspective view of ulnar member 1015 with bore 1230, in accordance with some embodiments of the present invention.

As shown in FIG. 14A, ulnar member 1015 may be formed from two separate pieces: a receptacle piece 1410 and a mounting piece 1420. Receptacle piece 1410 includes with two rails 1405. Bore 1230 is formed in receptable piece 1410 and configured to receive hook 1040. Mounting piece 1420 includes the screw holes used for affixing the ulnar member to the ulna bone and also includes tracks 1415 into which rails 1405 can be slid so as to hold receptacle piece 1410 on mounting piece 1420. In this manner, receptacle piece 1410 may be adjusted to have different overall lengths. Receptacle piece 1410 with different sizes or shapes of bore 1230 may also be used to optimize the performance of the DRUJ replacement. The screws and screw holes are the same as described in FIGS. 10-12. Receptacle piece 1410 is formed from a material selected from the group consisting of mobile polyethylene and pyrocarbon. Mounting piece 1420 is formed from a material selected from the group consisting of stainless steel and titanium. In some embodiments, the stainless steel and titanium may be impregnated with hydroxylapatite.

Figure 15:
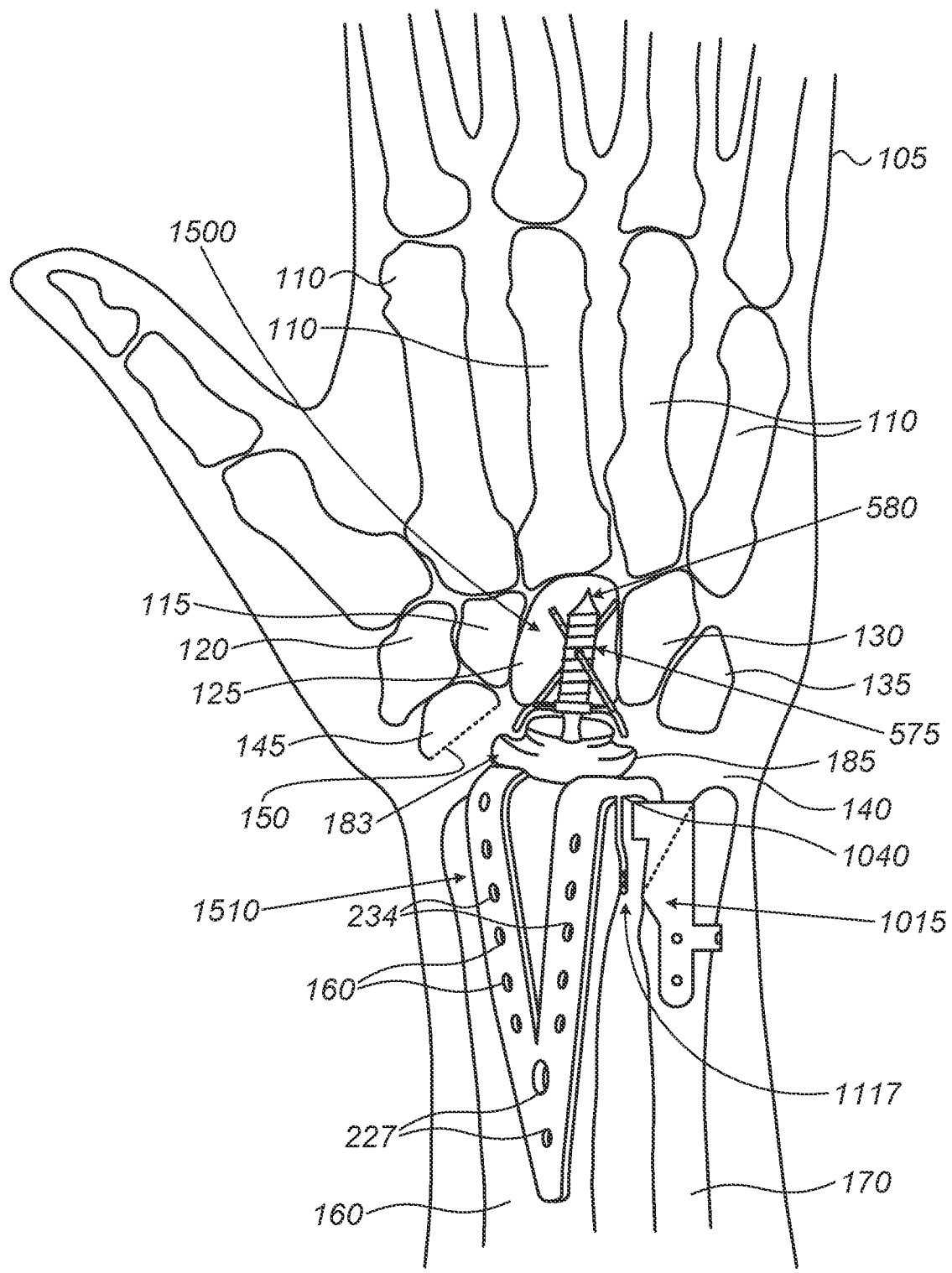
FIG. 15 schematically illustrates a dorsal view of a hand with a combination of a radiocarpal joint (RCJ) replacement and a distal radioulnar joint (DRUJ) replacement, in accordance with some embodiments of the present invention.

FIG. 15 schematically illustrates a dorsal view of hand 105 with a combination 1500 of a radiocarpal joint (RCJ) replacement and a distal radioulnar joint (DRUJ) replacement, in accordance with some embodiments of the present invention. In the event that the subject, or patient, requires both a RCJ and DRUJ replacement, the embodiments shown in FIGS. 5 and 10 may be combined as shown in FIG. 15. The description as to how the various members are affixed to the carpal capitate, radial and ulna bones is as described previously. However, radial member 155 is modified to include the elements of the sigmoidal member, namely hook 1040 and lower mounting bracket 1117 of sigmoidal member 1005.

Figure 16:
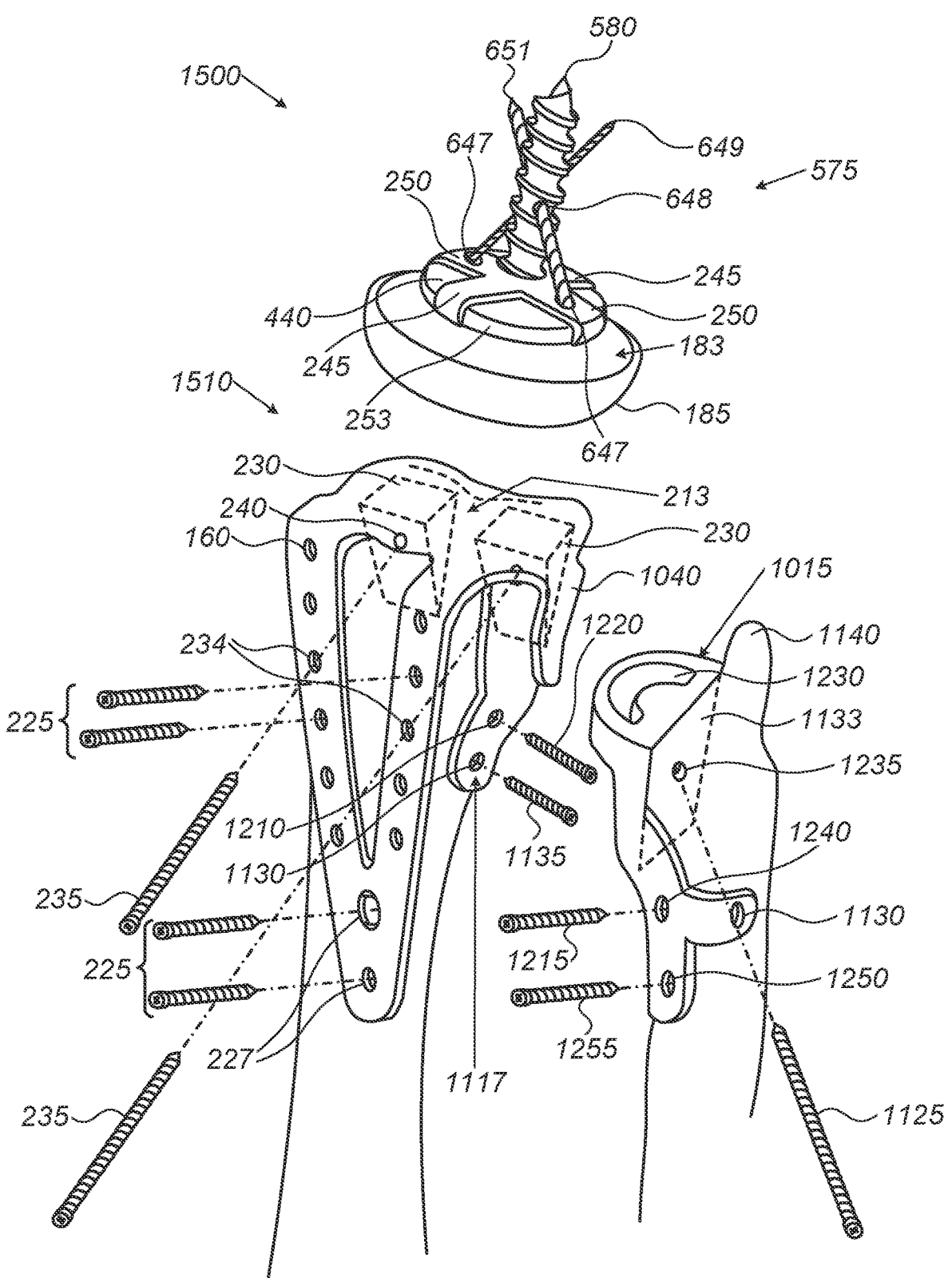
FIG. 16 schematically illustrates an exploded view of a combination of a radiocarpal joint (RCJ) replacement and a distal radioulnar joint (DRUJ) replacement, in accordance with some embodiments of the present invention.

FIG. 16 schematically illustrates an exploded view of combination 1500 of a radiocarpal joint (RCJ) replacement and a distal radioulnar joint (DRUJ) replacement, in accordance with some embodiments of the present invention. A modified radial member 1510 with hook 1040 and lower mounting bracket 1117 of sigmoidal member 1005 is affixed to radial bone 165. Ulnar member 1015 is affixed to ulna bone 170.

After implantation, radial resurfacing plate 213 of modified radial member 1510 with the concave surface is configured to be operably coupled to the convex surface of convex head 185 of carpal capitate member 575 so as to allow radial freedom of motion of the carpal capitate member with respect to the radial resurfacing plate of the RCJ replacement. Hook 1040 is inserted into bore 1230, which is configured to receive and retain the hook. The bore in the DRUJ replacement is shaped to allow relative movements between the radial bone and ulna bone so as to facilitate supination and pronation movement of the wrist. Note that either embodiment of carpal capitate member may be used in the RCJ replacement in FIGS. 15-16 (e.g., carpal capitate member 175 or carpal capitate member 575).

FIG. 17A schematically illustrates a first side view of modified radial member 1510, in accordance with some embodiments of the present invention.

FIG. 17B schematically illustrates a bottom view of modified radial member 1510 with hook 1040, in accordance with some embodiments of the present invention.

FIG. 17C schematically illustrates a second side view of modified radial member 1510 with hook 1040, in accordance with some embodiments of the present invention.

FIG. 17D schematically illustrates a top view of modified radial member 1510 with hook 1040, in accordance with some embodiments of the present invention.

FIG. 17E schematically illustrates a first perspective view of modified radial member 1510 with hook 1040, in accordance with some embodiments of the present invention.

FIG. 17F schematically illustrates a second perspective view of a modified radial member with hook 1040, in accordance with some embodiments of the present invention.

Modified radial member 1510 is identical to radial member 155 as shown in FIG. 3, with the exception that hook 1040 and lower mounting bracket 1117 from sigmoidal member 1105 are integrally formed in modified radial member 1510.

The wrist implants shown above may use implant fixtures affixed externally to the cortical bone tissue of the wrist bones (e.g., carpal capitate, radius, and ulna bones) so as to provide implant stability. Articular surfaces may be formed and/or attached to each of the implant fixtures such that when assembled, the movements of the joint articulating surfaces after implant assembly may closely resemble the anatomical movement of healthy joints. Moreover, pegs may be attached to the bottom side of the articulating surfaces (e.g., on the side of the articulating surfaces opposite the joint). The pegs may be pressed and implanted into the bone, for example into cancellous bone tissue, at the end of the bone for better self-enhancing implant stability. Screws passing through screw holes in the implant fixtures passing through the cortical bone tissue, for example, and into holes in the pegs may provide even greater stability so as to anchor the implant, for example, with a pyramid-like closed frame. The closed external frame joint resurfacing system fixation methods shown above for the radiocarpal and distal radioulnar joint replacement apparatus for implantation in a wrist of a subject and may thus be extended to other joint implants in the body.

Figures 18A, 18B, 18C, 18D:
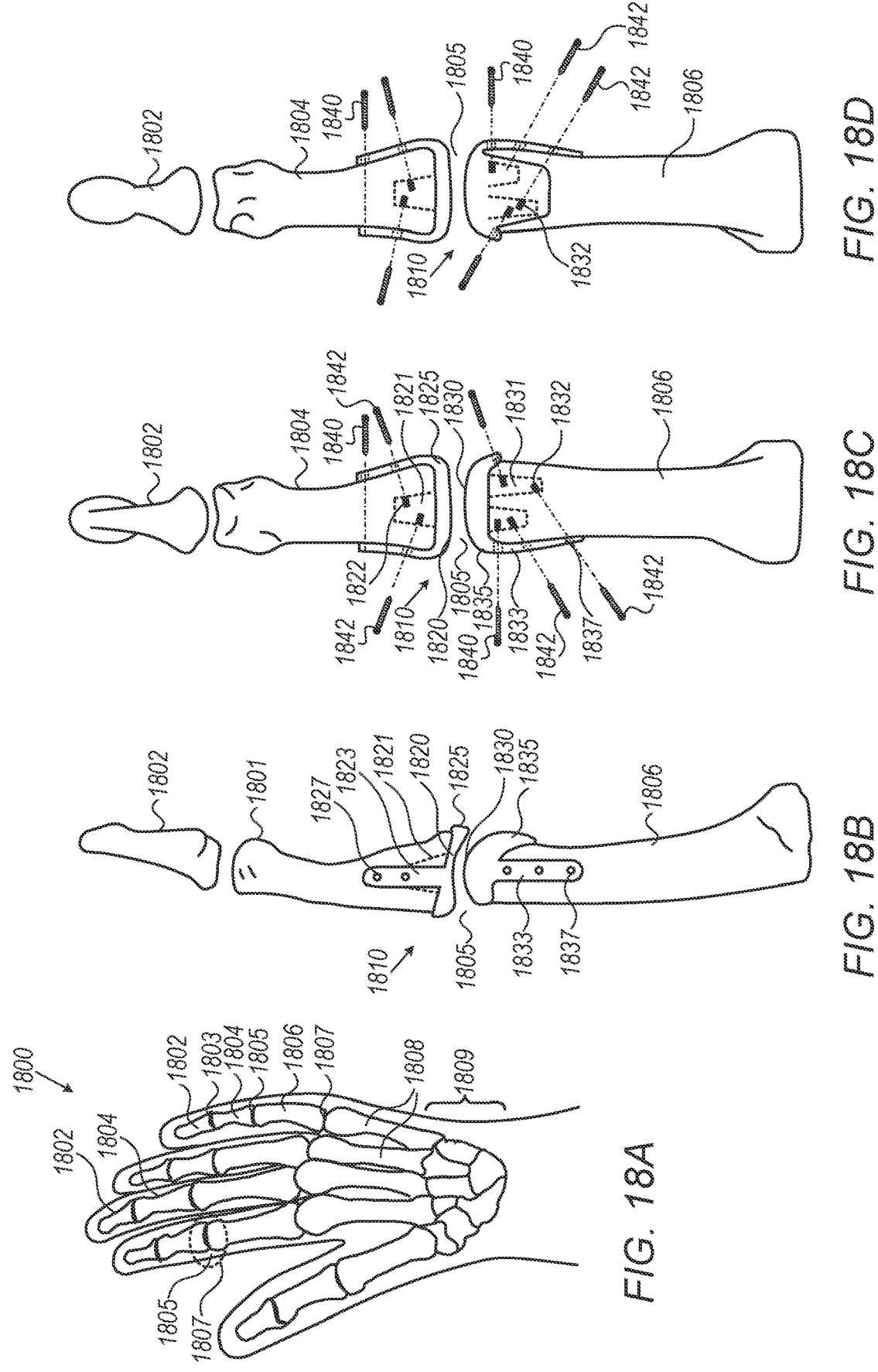
FIG. 18A schematically illustrates a dorsal view of hand bones, in accordance with some embodiments of the present invention.
FIG. 18B schematically illustrates a side view of a proximal interphalangeal joint (PIP) replacement, in accordance with some embodiments of the present invention.
FIG. 18C schematically illustrates a dorsal view of a proximal interphalangeal joint (PIP) replacement, in accordance with some embodiments of the present invention.
FIG. 18D schematically illustrates a palmar view of a proximal interphalangeal joint (PIP) replacement, in accordance with some embodiments of the present invention.

FIG. 18A schematically illustrates a dorsal view of hand bones 1800, in accordance with some embodiments of the present invention.

Hand bones 1800 of a human hand may include distal phalanges 1802, middle phalanges 1804, proximal phalanges 1806, metacarpals 1808, and carpals 1809. Joints between the finger bones may include a distal interphalangeal joint 1803 (DIP), a proximal interphalangeal joint 1805 (PIP), and a metacarpophalangeal joint 1807. Below is a description of embodiments of a joint replacement for implantation into PIP joint 1805 as shown in a circle 1807 of FIG. 18A.

FIG. 18B schematically illustrates a side view of a proximal interphalangeal joint (PIP) replacement 1810, in accordance with some embodiments of the present invention.

FIG. 18C schematically illustrates a dorsal view of proximal interphalangeal joint (PIP) replacement 1810, in accordance with some embodiments of the present invention.

FIG. 18D schematically illustrates a volar view of proximal interphalangeal joint (PIP) replacement 1810, in accordance with some embodiments of the present invention.

PIP replacement 1810 may include a middle phalange (MP) member 1825 attached to middle phalange 1804, and a proximal phalange (PP) member 1835 attached to proximal phalange 1806. MP member 1825 may include an MP fixture 1823 (e.g., one or more MP fixtures) externally affixed to cortical bone tissue along a longitudinal aspect of middle phalange 1804, and an MP resurfacing plate 1820 at the end of middle phalange 1804 proximal to PIP joint 1805. "Proximal" in the embodiments of FIGS. 18 and 19 refers, in the context of the present application, to the side of bone closest to the joint in which the joint replacement apparatus is implanted. For example, in the embodiments shown in FIGS. 18A-18D, proximal to the PIP joint 1805. Screws 1840 screwed through holes 1827 may be used to affix MP fixture 1823 externally to cortical bone tissue along a longitudinal aspect of middle phalange 1804.

PP member 1835 may include a PP fixture 1833 externally affixed to cortical bone tissue along a longitudinal aspect of proximal phalange 1806, and a PP resurfacing plate 1830 at the end of proximal phalange 1806 proximal to PIP joint 1805. Screws 1840 screwed through holes 1837 may be used, for example, to affix PP fixture 1833 externally to cortical bone tissue along a longitudinal aspect of proximal phalange 1806.

Attached to the side of MP resurfacing plate 1820 opposite to PIP joint 1805 are one or more MP pegs 1821 (e.g., one peg shown in FIGS. 18A-18D) for insertion into cancellous bone tissue in middle phalange 1804. Screws 1842 may be used to affix MP resurfacing plate 1820 to the end of middle phalange 1804 proximal to PIP joint 1805 by screwing screws 1842 into one or more MP peg holes 1822 in one or more MP pegs 1821. This provides additional implant stability.

Similarly, attached to the side of PP resurfacing plate 1830 opposite to PIP joint 1805 are one or more PP pegs 1831 for insertion into cancellous bone tissue in proximal phalange 1806. Screws 1842 may be used to affix PP fixture 1833 to the end of proximal phalange 1806 proximal to PIP joint 1805 by screwing screws 1842 into one or more PP peg holes 1832 in one or more respective PP pegs 1831.

In some embodiments of the present invention, after implantation each of MP resurfacing plate 1820 and PP resurfacing plate 1830 are shaped, to fit and to move together, so as to facilitate anatomical movements of the proximal interphalangeal joint (PIP) articulation (e.g., PIP joint 1805). In the context of the present patent application. "anatomical movements" is defined herein to mean that in coupling, bonding, connecting or otherwise holding together the components forming the joint replacement, implant, or prostheses, with two articulating resurfacing plate surfaces, the motion of the two articulating surfaces are identical, or most closely replicate, the same motions found in equivalent in vivo joint articulating surfaces of the joint articulation. Stated differently, the movements, or motions, of the joint replacement after implantation would most closely replicate the same movements, or motions, found equivalently in a normal (healthy) joint.

Figures 19A, 19B, 19C:
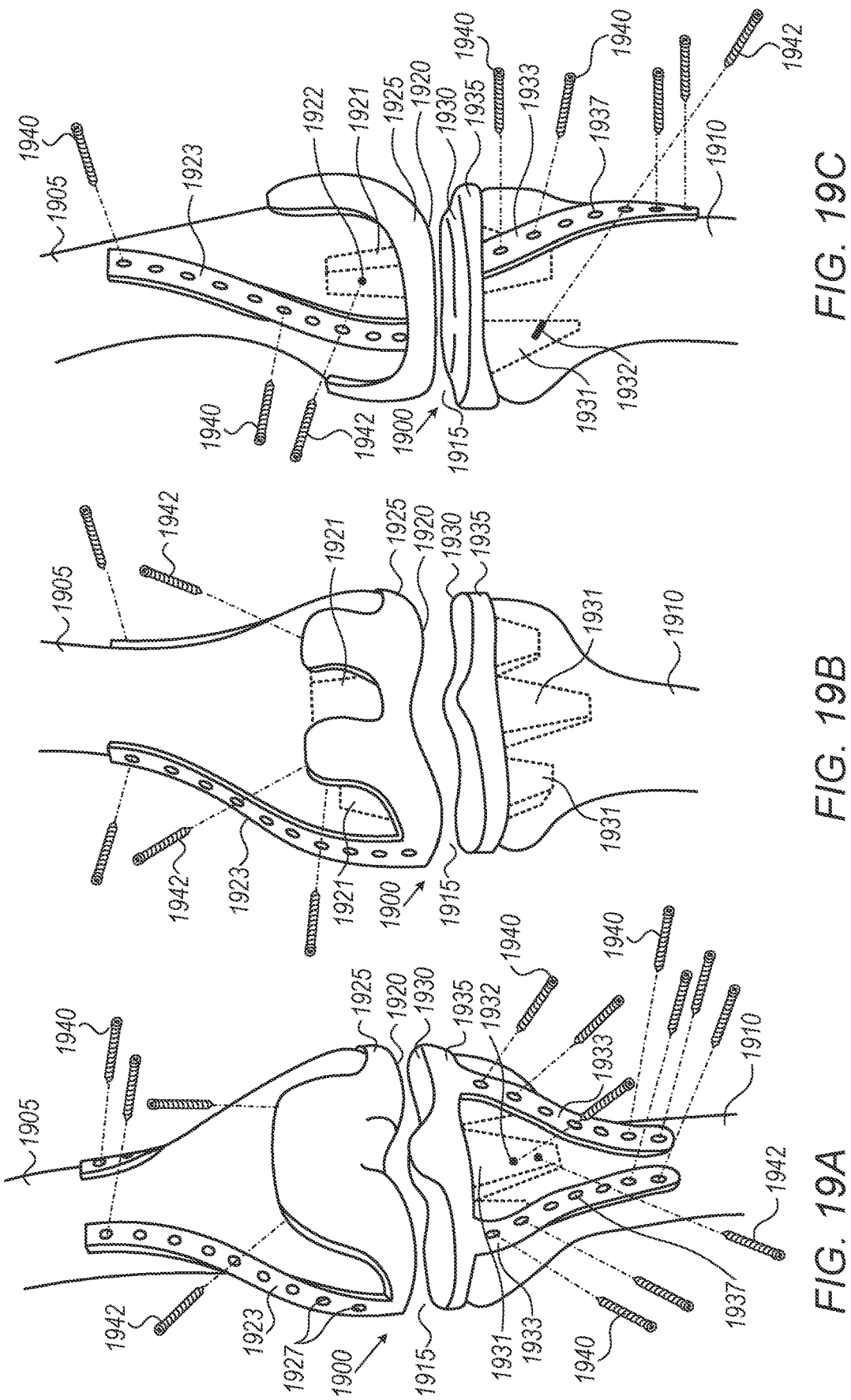
FIG. 19A schematically illustrates an anterior view of a tibiofemoral (TF) joint replacement, in accordance with some embodiments of the present invention.
FIG. 19B schematically illustrates a posterior view of a tibiofemoral (TF) joint replacement, in accordance with some embodiments of the present invention.
FIG. 19C schematically illustrates a side view of a tibiofemoral (TF) joint replacement, in accordance with some embodiments of the present invention.

FIG. 19A schematically illustrates an anterior view of a tibiofemoral (TF) joint replacement 1900, in accordance with some embodiments of the present invention.

FIG. 19B schematically illustrates a posterior view of tibiofemoral (TF) joint replacement 1900, in accordance with some embodiments of the present invention.

FIG. 19C schematically illustrates a side view of tibiofemoral (TF) joint replacement 1900, in accordance with some embodiments of the present invention.

A tibiofemoral joint (TF) 1915 of the knee is the articulation between a femur 1905 and a tibia 1910 bones of the human leg as shown in the different views in FIGS. 19A-19C.

TF replacement 1900 may include a femur member 1925 attached to femur 1905, and a tibia member 1935 attached to tibia 1910. Femur member 1925 may include a femur fixture 1923 (e.g., one or more femur members) externally affixed to cortical bone tissue along a longitudinal aspect of femur 1905, and a femur resurfacing plate 1920 at the end of femur 1905 proximal to TF joint 1915. Screws 1940 screwed through holes 1927 may be used to affix femur fixtures 1923, for example, externally affixed to cortical bone tissue along a longitudinal aspect of femur 1905.

Tibia member 1935 may include a tibia fixture 1933 externally affixed externally to cortical bone tissue along a longitudinal aspect of tibia 1910, and a tibia resurfacing plate 1930 at the end of tibia 1910 proximal to TF joint 1915. Screws 1940 screwed through holes 1937 may be used to affix tibia fixture 1933, for example, externally affixed to cortical bone tissue along a longitudinal aspect of tibia 1910.

Attached to the side of femur resurfacing plate 1920 opposite to TF joint 1915 are one or more femur pegs 1921 for insertion into cancellous bone tissue in femur 1905. Screws 1942 may be used to affix femur resurfacing plate 1920 to the end of femur 1905 proximal to TF joint 1915 by screwing screws 1942 through one or more femur peg holes 1922 through one or more respective femur pegs 1921.

Similarly, attached to the side of tibia resurfacing plate 1930 opposite to TF joint 1915 are one or more tibia pegs 1931 for insertion into cancellous bone tissue in tibia 1910. Screws 1942 may be used to affix tibia fixture 1933 to the end of tibia 1910 proximal to TF joint 1915 by screwing screws 1942 through one or more tibia peg holes 1932 through one or more respective tibia pegs 1931 so as to provide additional implant stability.

In some embodiments of the present invention, after implantation each of femur resurfacing plate 1920 and tibia resurfacing plate 1930 are shaped, to fit and to move together, so as to facilitate anatomical movements of the tibiofemoral joint (e.g., TF joint 1915).

In some embodiments of the present invention, a joint replacement apparatus for implantation into an articulation between a first and a second bone in a subject may include a first member configured to be affixed to an end of the first bone proximal to the articulation between the first bone and the second bone, the first member including one or more first member fixtures to be affixed externally to cortical bone tissue along a longitudinal aspect of the first bone, and a first resurfacing plate configured to be located at the end of the first bone. A second member configured to be affixed to an end of a second bone proximal to the articulation, the second member including one or more second member fixtures configured to be affixed externally to cortical bone tissue along a longitudinal aspect of the second bone, and a second resurfacing plate configured to be located at the end of the second bone. Each of the first and the second resurfacing plates are shaped, to fit and to move together, so as to facilitate anatomical movements of the articulation.

In some embodiments of the present invention, the one or more first member fixtures and the one or more are second member fixtures may be configured to be externally affixed to cortical bone tissue along a longitudinal aspect of the respective first and second bone by screwing screws into screw holes in each of the fixtures.

In some embodiments of the present invention, the first resurfacing plate and the second resurfacing plate may be configured to be affixed to the end of the respective first and second bone proximal to the articulation by screwing screws through screw holes respectively in the one or more first member fixtures and the one or more second member fixtures into peg holes in pegs attached respectively into the first or the second resurfacing plates. Note that the first or the second resurfacing plate, or both, may use screws screwed through holes in the fixtures, through the cortical bone tissue, and into the peg holes (e.g., for forming a closed frame for better implant stability).

In some embodiments of the present invention, the articulation may include a proximal interphalangeal joint, the first bone may include a middle phalange bone, and the second bone may include a proximal phalange bone.

In some embodiments of the present invention, the articulation may include a tibiofemoral joint, the first bone may include a femur bone, and the second bone may include a tibia bone.

In some embodiments of the present invention, the articulation may include a radiocarpal joint (RCJ), the first bone may include carpal capitate bone 175, the first member fixture may include cortical plate 247, the first resurfacing plate may include convex head 185 of bulbous component 183, the second bone may include radius bone 165, the second member fixture may include radial fixture 210, and the second resurfacing plate may include radial articular resurfacing plate 213.

In some embodiments, the resurfacing plates of FIGS. 18A-18D and 19A-19C may be formed from a polished metal surface.

In some embodiments, the fixtures may be formed from the group selected from polished stainless steel, titanium, and polyethylene.

Note that any of the methods described above in the RCJ and DRUJ joint replacements for affixing the fixtures and resurface plates to the bone may be applied to the embodiments shown in FIGS. 18A-18D and 19A-19C, for example, compression of the fixture longitudinally to the bone as described in the RCJ radial fixture by the use of oval screw holes 227 to affix the radial fixture to the radial bone.

Different embodiments are disclosed herein. Features of certain embodiments may be combined with features of other embodiments; thus, certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A radiocarpal joint replacement apparatus for implantation in a wrist of a subject, the apparatus comprising:

a radial member configured to be affixed to a portion of an end of the radial bone proximal to the wrist including a fixture to be affixed over a longitudinal aspect of the radial bone and a radial resurfacing plate having a substantially concave surface configured to be located at the end of the radial bone, the fixture including two joined bars;

a bulbous component;

a carpal capitate bone insert configured to be inserted and affixed into the carpal capitate bone;

wherein, a first joint is formed between the radial resurfacing plate and the bulbous component, and wherein a second joint is formed between the bulbous component and the carpal capitate bone insert.

2. The apparatus of claim 1, wherein a degree of freedom of the first joint is different from a degree of freedom of the second joint.

3. The apparatus of claim 1, wherein the bulbous component comprises a convex surface configured to operably couple with the substantially concave surface of the resurfacing plate.

4. The apparatus according to claim 1, wherein the carpal capitate bone insert comprises a dorsal cortical plate and an intraosseous stem, the intraosseous stem inserted into the carpal capitate bone, and the carpal capitate bone insert is affixed to the carpal capitate bone with screws inserted through holes in the dorsal cortical plate and the intraosseous stem.

5. The apparatus according to claim 1, wherein the carpal capitate bone insert comprises a screw threaded into the carpal capitate bone so as to affix the carpal capitate insert to the carpal capitate bone.

6. The apparatus according to claim 1, wherein the carpal capitate bone insert comprises an implant insertion element coated with hydroxylapatite.

7. The apparatus according to claim 1, wherein the bulbous component is formed from a material selected from the group consisting of polyethylene, ceramic, and pyrocarbon.

8. The apparatus according to claim 1, wherein the radial resurfacing plate is formed from a polished metal surface.

9. The apparatus according to claim 1, wherein the substantially concave surface of the radial resurfacing plate comprises a smooth surface.

\* \* \* \* \*